(12) United States Patent
Fulkerson et al.

(10) Patent No.: US 8,040,493 B2
(45) Date of Patent: Oct. 18, 2011

(54) THERMAL FLOW METER

(75) Inventors: Barry Neil Fulkerson, Longmont, CO (US); Mark F. Smith, Longmont, CO (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 12/575,449

(22) Filed: Oct. 7, 2009

(65) Prior Publication Data

US 2010/0116048 A1 May 13, 2010

Related U.S. Application Data

(63) Continuation-in-part of application No. 12/249,090, filed on Oct. 10, 2008.

(60) Provisional application No. 61/103,271, filed on Oct. 7, 2008, provisional application No. 60/979,113, filed on Oct. 11, 2007.

(51) Int. Cl.
*G01P 3/36* (2006.01)
(52) U.S. Cl. .......................................................... 356/28
(58) Field of Classification Search .................... 356/28, 356/28.5; 73/861.18, 861.27, 861.95; 600/309
See application file for complete search history.

(56) References Cited

U.S. PATENT DOCUMENTS

| | | |
|---|---|---|
| 2,328,381 A | 8/1943 | Jaffe |
| 3,388,803 A | 6/1968 | Scott |
| 3,746,175 A | 7/1973 | Markley |
| 3,803,913 A * | 4/1974 | Tracer ........................ 73/204.14 |
| 3,884,808 A | 5/1975 | Scott |
| 3,894,431 A | 7/1975 | Muston et al. |
| 3,902,490 A | 9/1975 | Jacobsen et al. |
| 3,989,622 A | 11/1976 | Marantz et al. |
| 3,994,799 A | 11/1976 | Yao et al. |
| 4,000,072 A | 12/1976 | Sato et al. |
| 4,071,444 A | 1/1978 | Ash et al. |
| 4,094,775 A | 6/1978 | Mueller |
| 4,118,314 A | 10/1978 | Yoshida |
| 4,209,392 A | 6/1980 | Wallace |
| 4,212,738 A | 7/1980 | Henne |
| 4,247,393 A | 1/1981 | Wallace |
| 4,267,040 A | 5/1981 | Schal |
| 4,269,708 A | 5/1981 | Bonomini et al. |
| 4,326,955 A | 4/1982 | Babb et al. |
| 4,348,283 A | 9/1982 | Ash |
| 4,368,737 A | 1/1983 | Ash |
| 4,387,777 A | 6/1983 | Ash |
| 4,402,694 A | 9/1983 | Ash et al. |
| 4,403,984 A | 9/1983 | Ash et al. |
| 4,413,988 A | 11/1983 | Handt et al. |
| 4,443,333 A | 4/1984 | Mahurkar |
| 4,469,593 A | 9/1984 | Ishihara et al. |
| 4,480,483 A | 11/1984 | McShane |

(Continued)

FOREIGN PATENT DOCUMENTS
WO PCT/US2009/059907 4/2010

*Primary Examiner* — Isam Alsomiri
(74) *Attorney, Agent, or Firm* — Novel IP

(57) ABSTRACT

A thermal flow meter for use in dialysis is described, that uses a thermal wave to generate a signal in the fluid for which the flow rate is to be measured. The phase angle of the thermal wave signal changes when traversing downstream. The phase difference between the signals received downstream, compared with a reference excitation source signal is measured, and used to determine the flow rate of the fluid.

20 Claims, 15 Drawing Sheets

U.S. PATENT DOCUMENTS

| | | | |
|---|---|---|---|
| 4,498,902 A | 2/1985 | Ash et al. | |
| 4,535,637 A * | 8/1985 | Feller | 73/861.77 |
| 4,559,039 A | 12/1985 | Ash et al. | |
| 4,563,170 A | 1/1986 | Aigner | |
| 4,581,141 A | 4/1986 | Ash | |
| 4,661,246 A | 4/1987 | Ash | |
| 4,765,907 A | 8/1988 | Scott | |
| 4,777,953 A | 10/1988 | Ash et al. | |
| 4,806,247 A | 2/1989 | Schoendorfer et al. | |
| 4,828,543 A | 5/1989 | Weiss et al. | |
| 4,831,884 A | 5/1989 | Drenthen | |
| 4,854,322 A | 8/1989 | Ash et al. | |
| 4,885,942 A | 12/1989 | Magori | |
| 4,897,189 A | 1/1990 | Greenwood et al. | |
| 4,914,819 A | 4/1990 | Ash | |
| 4,950,395 A | 8/1990 | Richalley | |
| 4,968,422 A | 11/1990 | Runge et al. | |
| 4,995,268 A | 2/1991 | Ash et al. | |
| 4,997,570 A | 3/1991 | Polaschegg | |
| 5,002,054 A | 3/1991 | Ash et al. | |
| 5,032,261 A | 7/1991 | Pyper | |
| 5,100,554 A | 3/1992 | Polaschegg | |
| 5,114,580 A | 5/1992 | Ahmad et al. | |
| 5,147,613 A | 9/1992 | Heilmann et al. | |
| 5,152,174 A | 10/1992 | LaBudde | |
| 5,198,335 A | 3/1993 | Sekikawa et al. | |
| 5,211,643 A | 5/1993 | Reinhardt et al. | |
| 5,230,341 A | 7/1993 | Polaschegg | |
| 5,277,820 A | 1/1994 | Ash | |
| 5,284,470 A | 2/1994 | Beltz | |
| 5,284,559 A | 2/1994 | Lim et al. | |
| 5,295,505 A | 3/1994 | Polaschegg et al. | |
| 5,304,349 A | 4/1994 | Polaschegg | |
| 5,308,315 A | 5/1994 | Khuri et al. | |
| 5,322,519 A | 6/1994 | Ash | |
| 5,360,445 A | 11/1994 | Goldowsky | |
| 5,385,005 A | 1/1995 | Ash | |
| D355,816 S | 2/1995 | Ash | |
| 5,391,143 A | 2/1995 | Kensey | |
| 5,405,315 A | 4/1995 | Khuri et al. | |
| 5,405,320 A | 4/1995 | Twardowski et al. | |
| 5,415,532 A | 5/1995 | Loughnane et al. | |
| 5,445,630 A | 8/1995 | Richmond | |
| 5,476,444 A | 12/1995 | Keeling et al. | |
| D370,531 S | 6/1996 | Ash et al. | |
| 5,536,412 A | 7/1996 | Ash | |
| 5,540,265 A | 7/1996 | Polaschegg et al. | |
| 5,545,131 A | 8/1996 | Davankov | |
| 5,577,891 A | 11/1996 | Loughnane et al. | |
| 5,580,460 A | 12/1996 | Polaschegg | |
| 5,614,677 A | 3/1997 | Wamsiedler et al. | |
| 5,616,305 A | 4/1997 | Mathieu | |
| 5,624,551 A | 4/1997 | Baumann et al. | |
| 5,632,897 A | 5/1997 | Mathieu | |
| 5,698,083 A | 12/1997 | Glass | |
| 5,711,883 A | 1/1998 | Folden et al. | |
| 5,713,850 A | 2/1998 | Heilmann et al. | |
| 5,725,773 A | 3/1998 | Polaschegg | |
| 5,725,776 A | 3/1998 | Kenley et al. | |
| 5,770,806 A | 6/1998 | Hiismaki | |
| 5,794,669 A | 8/1998 | Polaschegg et al. | |
| 5,858,186 A | 1/1999 | Glass | |
| 5,876,419 A | 3/1999 | Carpenter et al. | |
| 5,902,336 A | 5/1999 | Mishkin | |
| 5,906,978 A | 5/1999 | Ash | |
| 5,919,369 A | 7/1999 | Ash | |
| 5,944,684 A | 8/1999 | Roberts et al. | |
| 5,947,953 A | 9/1999 | Ash et al. | |
| 5,980,481 A | 11/1999 | Gorsuch | |
| 5,984,891 A | 11/1999 | Keilman et al. | |
| 6,042,561 A | 3/2000 | Ash et al. | |
| 6,117,100 A | 9/2000 | Powers et al. | |
| 6,117,122 A | 9/2000 | Din et al. | |
| 6,156,007 A | 12/2000 | Ash | |
| 6,168,578 B1 | 1/2001 | Diamond | |
| 6,190,349 B1 | 2/2001 | Ash et al. | |
| 6,196,922 B1 | 3/2001 | Hantschk et al. | |
| 6,196,992 B1 | 3/2001 | Keilman et al. | |
| 6,217,540 B1 | 4/2001 | Yazawa et al. | |
| 6,254,567 B1 | 7/2001 | Treu et al. | |
| 6,264,680 B1 | 7/2001 | Ash | |
| 6,287,516 B1 | 9/2001 | Matson et al. | |
| 6,303,036 B1 | 10/2001 | Collins et al. | |
| 6,325,774 B1 | 12/2001 | Bene et al. | |
| 6,332,985 B1 | 12/2001 | Sherman et al. | |
| 6,348,162 B1 | 2/2002 | Ash | |
| 6,406,631 B1 | 6/2002 | Collins et al. | |
| 6,409,699 B1 | 6/2002 | Ash | |
| 6,471,872 B2 | 10/2002 | Kitaevich et al. | |
| 6,487,904 B1 * | 12/2002 | Myhre | 73/204.12 |
| 6,491,673 B1 | 12/2002 | Palumbo et al. | |
| 6,497,675 B1 | 12/2002 | Davankov | |
| 6,551,513 B2 | 4/2003 | Nikaido et al. | |
| 6,554,789 B1 | 4/2003 | Brugger et al. | |
| 6,561,997 B1 | 5/2003 | Weitzel et al. | |
| 6,572,576 B2 | 6/2003 | Brugger et al. | |
| 6,572,641 B2 | 6/2003 | Brugger et al. | |
| 6,579,253 B1 | 6/2003 | Burbank et al. | |
| 6,579,460 B1 | 6/2003 | Willis et al. | |
| 6,582,385 B2 | 6/2003 | Burbank et al. | |
| 6,589,482 B1 | 7/2003 | Burbank et al. | |
| 6,595,943 B1 | 7/2003 | Burbank | |
| 6,610,036 B2 | 8/2003 | Branch et al. | |
| 6,623,470 B2 | 9/2003 | Munis et al. | |
| 6,627,164 B1 | 9/2003 | Wong | |
| 6,632,192 B2 | 10/2003 | Gorsuch et al. | |
| 6,638,477 B1 | 10/2003 | Treu et al. | |
| 6,638,478 B1 | 10/2003 | Treu et al. | |
| 6,649,063 B2 | 11/2003 | Brugger et al. | |
| 6,673,314 B1 | 1/2004 | Burbank et al. | |
| 6,681,624 B2 * | 1/2004 | Furuki et al. | 73/204.13 |
| 6,685,664 B2 | 2/2004 | Levin et al. | |
| 6,702,561 B2 | 3/2004 | Stillig et al. | |
| 6,706,007 B2 | 3/2004 | Gelfand et al. | |
| 6,730,266 B2 | 5/2004 | Matson et al. | |
| 6,743,193 B2 | 6/2004 | Brugger et al. | |
| 6,758,975 B2 | 7/2004 | Peabody et al. | |
| 6,776,912 B2 | 8/2004 | Baurmeister | |
| 6,796,955 B2 | 9/2004 | O'Mahony et al. | |
| 6,818,196 B2 | 11/2004 | Wong | |
| 6,830,553 B1 | 12/2004 | Burbank et al. | |
| 6,841,172 B1 | 1/2005 | Ash | |
| 6,843,779 B1 | 1/2005 | Andrysiak et al. | |
| 6,852,090 B2 | 2/2005 | Burbank et al. | |
| 6,872,346 B2 | 3/2005 | Stillig | |
| 6,878,283 B2 | 4/2005 | Thompson | |
| 6,890,315 B1 | 5/2005 | Levin et al. | |
| 6,955,655 B2 | 10/2005 | Burbank et al. | |
| 6,958,049 B1 | 10/2005 | Ash | |
| 6,960,179 B2 | 11/2005 | Gura | |
| 6,960,328 B2 | 11/2005 | Bortun et al. | |
| 6,979,309 B2 | 12/2005 | Burbank et al. | |
| 7,004,924 B1 | 2/2006 | Brugger et al. | |
| 7,033,498 B2 | 4/2006 | Wong | |
| 7,040,142 B2 | 5/2006 | Burbank | |
| 7,087,026 B2 * | 8/2006 | Callister et al. | 600/526 |
| 7,087,033 B2 | 8/2006 | Brugger et al. | |
| 7,101,519 B2 | 9/2006 | Wong | |
| 7,112,273 B2 | 9/2006 | Weigel et al. | |
| 7,115,095 B2 | 10/2006 | Eigler et al. | |
| 7,135,156 B2 | 11/2006 | Hai et al. | |
| 7,144,386 B2 | 12/2006 | Korkor et al. | |
| 7,147,613 B2 | 12/2006 | Burbank et al. | |
| 7,169,303 B2 | 1/2007 | Sullivan et al. | |
| 7,175,809 B2 | 2/2007 | Gelfand et al. | |
| 7,214,312 B2 | 5/2007 | Brugger et al. | |
| 7,226,538 B2 | 6/2007 | Brugger et al. | |
| 7,241,272 B2 | 7/2007 | Karoor et al. | |
| 7,252,767 B2 | 8/2007 | Bortun et al. | |
| 7,267,658 B2 | 9/2007 | Treu et al. | |
| 7,270,015 B1 * | 9/2007 | Feller | 73/861.95 |
| 7,273,465 B2 | 9/2007 | Ash | |
| 7,276,042 B2 | 10/2007 | Polaschegg et al. | |
| 7,300,413 B2 | 11/2007 | Burbank et al. | |
| 7,309,323 B2 | 12/2007 | Gura et al. | |
| 7,337,674 B2 | 3/2008 | Burbank et al. | |
| 7,338,460 B2 | 3/2008 | Burbank et al. | |

| | | | | | | |
|---|---|---|---|---|---|---|
| 7,347,849 B2 | 3/2008 | Brugger et al. | | 2008/0051689 A1 | 2/2008 | Gura et al. |
| 7,351,218 B2 | 4/2008 | Bene | | 2008/0058696 A1 | 3/2008 | Gura et al. |
| 7,387,022 B1 * | 6/2008 | Korniyenko et al. ...... 73/204.11 | | 2008/0065006 A1 | 3/2008 | Roger et al. |
| 7,597,677 B2 | 10/2009 | Gura et al. | | 2008/0195021 A1 | 8/2008 | Roger et al. |
| 7,645,253 B2 | 1/2010 | Gura et al. | | 2008/0195060 A1 | 8/2008 | Roger et al. |
| 2002/0068364 A1 | 6/2002 | Arai et al. | | 2008/0217245 A1 | 9/2008 | Rambod et al. |
| 2002/0085951 A1 | 7/2002 | Gelfand et al. | | 2009/0079578 A1 | 3/2009 | Dvorsky et al. |
| 2002/0112609 A1 | 8/2002 | Wong | | 2009/0080757 A1 | 3/2009 | Roger et al. |
| 2003/0128125 A1 | 7/2003 | Burbank et al. | | 2009/0082646 A1 | 3/2009 | Bouton |
| 2003/0236482 A1 | 12/2003 | Gorsuch et al. | | 2009/0082647 A1 | 3/2009 | Busby |
| 2005/0150309 A1 | 7/2005 | Beard | | 2009/0082649 A1 | 3/2009 | Muller et al. |
| 2006/0122552 A1 | 6/2006 | O'Mahony | | 2009/0082653 A1 | 3/2009 | Rohde |
| 2006/0241543 A1 | 10/2006 | Gura | | 2009/0082676 A1 | 3/2009 | Bennison |
| 2007/0060786 A1 | 3/2007 | Gura et al. | | 2009/0101552 A1 | 4/2009 | Fulkerson et al. |
| 2007/0161113 A1 | 7/2007 | Ash | | 2009/0105627 A1 | 4/2009 | Rohde |
| 2007/0179425 A1 | 8/2007 | Gura et al. | | 2009/0120864 A1 | 5/2009 | Fulkerson et al. |
| 2008/0006570 A1 | 1/2008 | Gura et al. | | 2010/0022936 A1 | 1/2010 | Gura et al. |
| 2008/0021366 A1 | 1/2008 | Gura et al. | | 2010/0094193 A1 | 4/2010 | Gura et al. |
| 2008/0041136 A1 | 2/2008 | Kopelman et al. | | * cited by examiner | | |

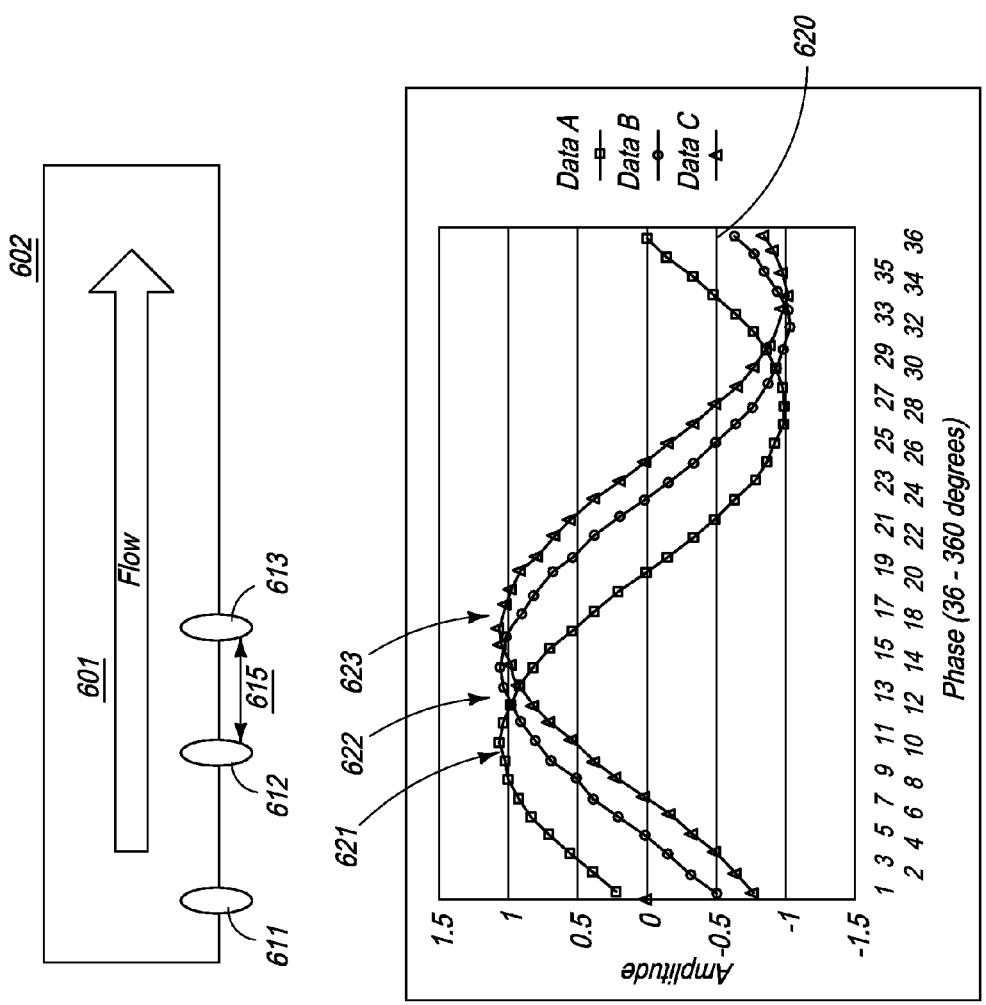

|  | Symbol | Equation | Units | Value | Value | Value | Value | Value | Value | Value | Value |
|---|---|---|---|---|---|---|---|---|---|---|---|
| 701 Flow rate | Q | | mL/min | 600.0 | 500.0 | 400.0 | 300.0 | 200.0 | 100.0 | 50.0 | 25.0 |
| 702 Fluid Velocity | V | | mm/s | 416.67 | 347.22 | 277.78 | 208.33 | 138.39 | 69.44 | 34.72 | 17.36 |
| 703 Probe Separation | d | | mm | 15.0 | 15.0 | 15.0 | 15.0 | 15.0 | 15.0 | 15.0 | 15.0 |
| 704 Travel Time | t | | sec | 0.0360 | 0.043 | 0.054 | 0.072 | 0.108 | 0.216 | 0.432 | 0.864 |
| 705 Excitation Frequency | f | | Hz | 27.778 | 23.148 | 18.519 | 13.889 | 9.259 | 4.630 | 2.315 | 1.157 |
| 706 Receiver Amplitude | $R_P$ | | | 0.00 | 0.00 | 0.00 | 0.00 | 0.00 | 0.00 | 0.00 | 0.00 |
|  |  |  |  | 18.00E-3 | 21.60E-3 | 27.00E-3 | 36.00E-3 | 54.00E-3 | 108.00E-3 | 216.00E-3 | 432.00E-3 |

FIG. 7a

|  | Symbol | Equation | Units | Value | Value | Value | Value | Value | Value | Value | Value |
|---|---|---|---|---|---|---|---|---|---|---|---|
| 801 Flow rate | Q |  | mL/min | 600.0 | 500.0 | 400.0 | 300.0 | 200.0 | 100.0 | 50.0 | 25.0 |
| 802 Fluid Velocity | V |  | mm/s | 416.67 | 347.22 | 277.78 | 208.33 | 138.39 | 69.44 | 34.72 | 17.36 |
| 803 Probe Separation | d |  | mm | 15.0 | 15.0 | 15.0 | 15.0 | 15.0 | 15.0 | 15.0 | 15.0 |
| 804 Travel Time | t |  | sec | 0.0360 | 0.043 | 0.054 | 0.072 | 0.108 | 0.216 | 0.432 | 0.864 |
| 805 Harmonic |  |  |  | 1.000 |  |  |  |  |  |  |  |
| 806 Excitation Frequency | f |  | Hz | 1.157 | 1.157 | 1.157 | 1.157 | 1.157 | 1.157 | 1.157 | 1.157 |
| 807 Receiver Amplitude | $R_P$ |  |  | 0.26 | 0.31 | 0.38 | 0.50 | 0.71 | 1.00 | 0.00 | 0.00 |
|  |  |  |  | 18.00E-3 | 21.60E-3 | 27.00E-3 | 36.00E-3 | 54.00E-3 | 108.00E-3 | 216.00E-3 | 432.00E-3 |

| | Symbol | Equation | Units | Value | Value | Value | Value | Value | Value | Value | Value |
|---|---|---|---|---|---|---|---|---|---|---|---|
| 901 Flow rate | Q | | mL/min | 600.0 | 500.0 | 400.0 | 300.0 | 200.0 | 100.0 | 50.0 | 25.0 |
| Flow rate | Q | | mL/sec | 10.00 | 8.333 | 6.667 | 5.000 | 3.333 | 1.667 | 0.833 | 0.417 |
| Flow rate | Q | | mm³/sec | 10000 | 8333 | 6667 | 5000 | 3333 | 1667 | 833 | 417 |
| 902 Channel Height | h | | mm | 3.00 | 3.00 | 3.00 | 3.00 | 3.00 | 3.00 | 3.00 | 3.00 |
| Channel Height | h | | m | 3.000E-3 | 3.000E-3 | 3.000E-3 | 3.000E-3 | 3.000E-3 | 3.000E-3 | 3.000E-3 | 3.000E-3 |
| 903 Channel Width | w | | mm | 8.00 | 8.00 | 8.00 | 8.00 | 8.00 | 8.00 | 8.00 | 8.00 |
| Channel Width | w | | m | 8.00E-3 | 8.00E-3 | 8.00E-3 | 8.00E-3 | 8.00E-3 | 8.00E-3 | 8.00E-3 | 8.00E-3 |
| 904 Channel Length | L | | mm | 50.0 | 50.0 | 50.0 | 50.0 | 50.0 | 50.0 | 50.0 | 50.0 |
| Channel Length | L | | m | 0.05 | 0.05 | 0.05 | 0.05 | 0.05 | 0.05 | 0.05 | 0.05 |
| 905 Channel Area | A | | mm² | 24.00 | 24.00 | 24.00 | 24.00 | 24.00 | 24.00 | 24.00 | 24.00 |
| 906 Hydraulic Diameter | $D_h$ | 2hw/(h+w) | mm | 4.36 | 4.36 | 4.36 | 4.36 | 4.36 | 4.36 | 4.36 | 4.36 |
| Hydraulic Diameter | $D_h$ | 2hw/(h+w) | m | 4.364E-3 | 4.364E-3 | 4.364E-3 | 4.364E-3 | 4.364E-3 | 4.364E-3 | 4.364E-3 | 4.364E-3 |
| 907 Velocity | V | | mm/sec | 416.7 | 347.2 | 277.9 | 208.3 | 138.9 | 69.4 | 34.7 | 17.4 |
| Velocity | V | | m/sec | 0.417 | 0.347 | 0.278 | 0.208 | 0.139 | 0.069 | 0.035 | 0.017 |
| 908 Water | | | | | | | | | | | |
| Density | ρ | | kg/m³ | 998 | 998 | 998 | 998 | 998 | 998 | 998 | 998 |
| Dynamic Viscosity | μ | | Kg/(m*s) | 1.000E-3 | 1.000E-3 | 1.000E-3 | 1.000E-3 | 1.000E-3 | 1.000E-3 | 1.000E-3 | 1.000E-3 |
| Kinematic Viscosity | ν | μ/ρ | m²/s | 1.002E-6 | 1.002E-6 | 1.002E-6 | 1.002E-6 | 1.002E-6 | 1.002E-6 | 1.002E-6 | 1.002E-6 |
| 909 Reynolds Number | $Re_{Dh}$ | $VD_h/ν$ | | 1815 | 1512 | 1210 | 907 | 605 | 302 | 151 | 76 |

|   | Symbol | Equation | Units | Value |
|---|---|---|---|---|
| Excitation Probe |   |   |   |   |
| Material: Brass |   |   |   |   |
| Density | $\rho$ |   | $Kg/m^3$ | 8500 |
| Thermal Conductivity | $\kappa$ |   | $W/mK$ | 1.090 |
| Specific Heat | $\overline{C}_p$ |   | $J/KgK$ | 0.380 |
| Size |   |   |   |   |
| Diameter | $d$ |   | $mm$ | 2.000 |
| Length | $l$ |   | $mm$ | 6.000 |
| Volume | $V$ |   | $mm^3$ | 18.85 |
| Volume | $V$ |   | $m^3$ | 18.85E-9 |
| Mass | $M$ |   | $Kg$ | 160.2E-6 |
| Exposed Surface Area | $A_e$ |   | $mm^2$ | 6.849 |
| Exposed Surface Area | $A_e$ |   | $m$ | 6.849E-3 |
| Convection Coefficient | $h$ |   | $W/(m^2K)$ | 15.0 |
| Thermal Time Constant | $\tau_t$ |   | $sec$ | 593E-6 |

FIG. 10

THERMAL FLOW METER

CROSS-REFERENCE

The present invention relies upon U.S. Patent Provisional Application No. 61/103,271, filed on Oct. 7, 2008, for priority and is a continuation-in-part of U.S. patent application Ser. No. 12/249,090, filed on Oct. 10, 2008 and which relies on U.S. Patent Provisional Application No. 60/979,113, filed on Oct. 11, 2007, for priority. All of the aforementioned applications are herein incorporated by reference.

FIELD OF THE INVENTION

The present invention generally relates to the field of systems and methods for fluid flow rate measurement, and, more specifically, to a thermal fluid flow meter for use in a dialysis manifold system.

BACKGROUND OF THE INVENTION

Fluid flow meters operate based upon the principle that the propagation velocity of a wave in a fluid, as determined by measuring the phase shift of the signal, is indicative of the velocity of the fluid. U.S. Pat. No. 3,894,431 to Muston, et al discloses determining fluid flow rates "by transmitting ultrasonic pulses in both directions along a path through the fluid aligned with the direction in which velocity component is to be measured. Transmission of, and measurement upon, pulses in the two directions are controlled by a master clock pulse generator. The frequency of a first variable frequency oscillator is adjusted to fit N pulses exactly into the timer period for flight of an ultrasonic pulse along the path in one direction. The frequency of a second variable frequency oscillator is adjusted to fit N pulses exactly into the time period for flight of an ultrasonic pulse along the path in the opposite direction. The difference frequency is proportional to velocity component. This system may be combined with a limited sing-around system to improve resolution, at the expense of the time response."

U.S. Pat. No. 4,885,942 to Magori discloses using "the phase difference method wherein two ultrasound transducers W1 and W2 are mounted offset but aligned with each other in a tube through which the velocity of flow is to be measured wherein both of the ultrasound transducers are excited in a pulse manner by an oscillator OS2 and wherein receiving amplifiers V1 and V2 are, respectively, associated with the ultrasound transducers W1 and W2. Evaluation devices are connected after amplifier V1 and V2 such that the phase relationship of the signals at the outputs of the receiving amplifiers V1 and V2 is determined during the reception of ultrasound signals. The phase relationship between the signals at the ultrasound transducers is also determined during transmission of ultrasound signals and this phase difference is used as a reference during reception of ultrasound signals."

U.S. Patent Publication No. 2006/0106308 describes use of thermal measurements to detect and/or measure the reestablishment of blood flow during a clot dissolution treatment. A catheter 10 is positioned through a clot 90 at a treatment site 88 in a patient's vasculature 86. The catheter 10 includes at least an upstream thermal source 120 and a downstream thermal detector 122. When the thermal source 120 supplies thermal energy into the surrounding environment, a "thermal pulse" 124 is created therein. As the thermal pulse 124 propagates downstream, the characteristics of the thermal pulse 124 will change, which can be measured and analyzed using the thermal detector, thereby providing information about blood flow at the treatment site.

U.S. Patent Publication No. 2003/0056585 describes a thermal flow meter with a flow rate detecting unit containing a heating element, a flow rate detecting temperature sensing element and a flow rate detecting electroconductive heat transfer member extending into a fluid flow passage, which are disposed so as to enable heat transfer therebetween, the flow rate detecting temperature sensing element varying in electrical characteristic value in accordance with flow of a fluid in the fluid flow passage through heat exchange with the fluid in the fluid flow passage which is carried out through the flow rate detecting electroconductive heat transfer member; and a fluid temperature detecting unit containing a fluid temperature detecting temperature sensing element and a fluid temperature detecting electroconductive heat transfer member extending into the fluid flow passage, which are disposed so as to enable heat transfer therebetween, the fluid temperature detecting temperature sensing element varying in electrical characteristic value in accordance with the temperature of the fluid through heat exchange with the fluid in the fluid flow passage, wherein a flow rate of the fluid is detected on the basis of the electrical characteristic value of the flow rate detecting temperature sensing element and the electrical characteristic value of the fluid temperature detecting temperature sensing element, and fluid discrimination is effected by determining a conductivity between the flow rate detecting electroconductive heat transfer member and the fluid temperature detecting electroconductive heat transfer member. All of the aforementioned patents and published applications are herein incorporated by reference.

These aforementioned prior art flow meters often suffer from excessive noise and may have limited efficacy where space around the flowing fluid is limited (such as in conduits of small diameters). These conditions are typically true for medical applications and are particularly so in extracorporeal blood processing systems such as hemodialysis, hemofiltration and hemodiafiltration systems.

Accordingly, there is need in the art for a thermal flow meter that has improved accuracy and efficacy. There is also a need in the art for a thermal flow meter that has decreased sensitivity to noise and signal dispersion. Finally, there is a need in the art for a thermal flow meter that can be readily implemented in a manifold, does not require expensive, non-disposable materials, and can generate a signal that can be readily, and easily, filtered.

SUMMARY OF THE INVENTION

In one embodiment, the present invention is directed toward a flow rate sensor for sensing the flow rate of a fluid passing through a channel, comprising a) an excitation probe having a body and a contact surface, wherein said excitation probe is physically positioned within said channel; b) a receiver probe having a body and a contact surface, wherein said receiver probe is physically positioned within said channel and wherein said receiver probe senses a thermal wave within said fluid; c) a reference signal generator, wherein said reference signal generator outputs a reference signal; d) a heat source, wherein said heat source receives said reference signal from said reference signal generator, is configured to thermally engage with said excitation probe, and generates a first thermal signal, having a frequency derived from said reference signal; e) a temperature sensor, wherein said temperature sensor is configured to thermally engage with said receiver probe, and generates a second thermal signal, having a frequency derived from said thermal wave; f) a multiplier for receiving an input signal from said reference signal generator and for receiving said second thermal signal and for outputting a third signal; and g) a low pass filter for receiving a fourth signal, wherein said fourth signal is a function of the third signal, and for receiving an input signal from said reference signal generator, wherein said low pass filter modulates its cutoff frequency based upon the input signal from said reference signal generator.

Optionally, the receiver probe is separated from said excitation probe by a distance of less than two inches. The flow rate sensor further comprises an amplifier for amplifying said third signal and generating said fourth signal. The channel area is in the range of 3 mm$^2$ to 65 mm$^2$. The body of said receiver probe or excitation probe has a diameter in the range of 0.03 inches to 0.15 inches. The contact surface of said receiver probe or excitation probe has a diameter in the range of 0.025 inches to 0.2 inches. The excitation probe and receiver probe are embedded into a manifold and wherein the contact surfaces of said receiver probe or excitation probe are externally exposed. The receiver probe comprises a thermistor. The flow rate sensor has an operative sensing range between 20 mL/min to 600 mL/min. The low pass filter generates a filtered signal and wherein the reference signal generator generates said reference signal based, at least in part, on said filtered signal. The flow rate sensor dynamically adjusts said reference signal in order to maintain a constant phase.

In another embodiment, the present invention is directed toward a manifold comprising a flow rate sensor for sensing the flow rate of a fluid passing through a channel having a hydraulic diameter in a range of 1.5 mm to 7.22 mm, comprising a) at least two probes, each having a body embedded into a first surface of said manifold and within said channel and each having a contact surface positioned on a surface of said manifold, wherein a second of said at least two probes senses a thermal wave within said fluid; b) a reference signal generator, wherein said reference signal generator outputs a reference signal; c) a heat source, wherein said heat source receives said reference signal from said reference signal generator, is configured to thermally engage with a first of said at least two probes, and generates a first thermal signal, having a phase derived from said reference signal; d) a temperature sensor, wherein said temperature sensor is configured to thermally engage with said second probe, and generates a second thermal signal, having a phase derived from said thermal wave; e) a multiplier for receiving an input signal from said reference signal generator and for receiving said second thermal signal and for outputting a third signal; and f) a low pass filter for receiving a fourth signal, wherein said fourth signal is a function of the third signal, and for receiving an input signal from said reference signal generator, wherein said low pass filter modulates its cutoff frequency based upon the input signal from said reference signal generator.

Optionally, the second probe is separated from said excitation probe by a distance of less than two inches. The manifold further comprises an amplifier for amplifying said third signal and generating said fourth signal. The body of each of said at least two probes has a diameter in the range of 0.03 inches to 0.15 inches. The contact surface of each of said at least two probes has a diameter in the range of 0.025 inches to 0.2 inches. The second probe comprises a thermistor. The low pass filter generates a filtered signal and wherein the reference signal generator generates said reference signal based, at least in part, on said filtered signal. The flow rate sensor dynamically adjusts said reference signal in order to maintain a constant frequency. The flow rate sensor dynamically adjusts said reference signal in order to maintain a constant phase.

BRIEF DESCRIPTION OF THE DRAWINGS

These and other features and advantages of the present invention will be appreciated, as they become better understood by reference to the following detailed description when considered in connection with the accompanying drawings, wherein:

FIG. 6a illustrates a schematic for the operation of a thermal flow meter of the present invention;

FIG. 6b depicts the relative phases of the thermal wave based on the placement of a contact and downstream detectors;

FIG. 7a is a table illustrating the range of excitation frequency that is dynamically adjusted to maintain a constant phase shift;

FIG. 7b illustrates the output of the phase sensitive detector for the values specified in FIG. 7a;

FIG. 8a illustrates a table detailing values of various parameters when the excitation frequency is maintained constant;

FIG. 9 illustrates a table delineating an exemplary set of optimized design parameters;

FIG. 10 is a table illustrating another set of exemplary design parameters for the excitation and receiver probes;

DETAILED DESCRIPTION OF THE INVENTION

Figure 1:
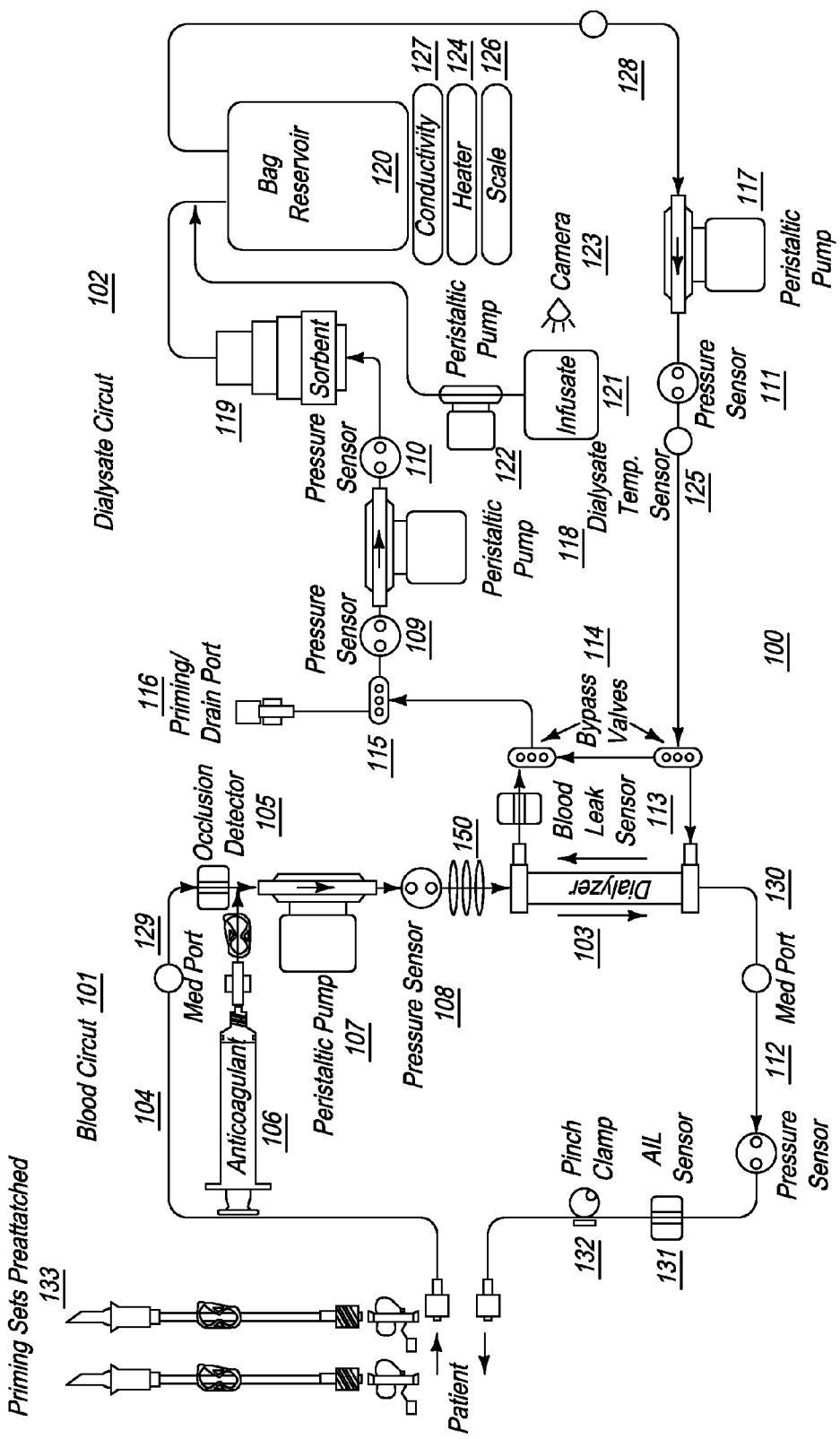
FIG. 1 is a diagram of a dialysis circuit with a flow rate sensor of the present invention included therein.

While the present invention may be embodied in many different forms, for the purpose of understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribe treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The present invention is a flow meter which can be used or implemented in any fluidic channel, tube, cell, passage, or opening. Such channels include: tubing in medical devices, manifolds in medical devices, and other industrial or commercial applications. The present invention is particularly well suited to sensing temperature levels and changes in applications where the fluid flow rate is between 10 mL/min to 1000 mL/min, particularly 20 mL/min to 600 mL/min. Additionally, the present invention is particularly well suited to sensing temperature levels and changes in applications where the flow can be generally characterized as laminar, as opposed to turbulent flow. Additionally, the present invention is particularly well suited to sensing temperature levels and changes in applications where the fluid involved has a density in the range of 800 to 1200 $kg/m^3$, and more preferably 1000 $kg/m^3$, a dynamic viscosity in the range of 0.001 kg/(m*s), and/or a kinematic viscosity in the range of $1.002 \times 10^{-6}$ $m^2/s$. Finally, the present invention is particularly well suited to sensing temperature levels and changes in applications where the fluid flow can be characterized with a Reynolds number in the range of 50 to 2500. Below, the present invention is specifically described in relation to use in dialysis machines, portable dialysis machines, extracorporeal blood circuits, and disposable manifolds.

The present invention is a novel thermal signal based flow meter that has the ability to generate a thermal signal directly in the fluid to be monitored. The flow meter of the present invention provides flow measurement with improved accuracy, and reduced susceptibility to noise generated by signal dispersion in prior art implementations. It is further contemplated the present flow meter can be incorporated into the structure of a disposable manifold used in medical applications, particularly dialysis machines. In particular, the present flow meter can be incorporated into the manifold structures and devices disclosed in U.S. patent application Ser. No. 12/237,914, entitled Manifolds for Use in Conducting Dialysis and filed on Sep. 25, 2008, and U.S. patent application Ser. No. 12/245,397, entitled Wearable Dialysis Methods and Devices and filed on Oct. 3, 2008, which are incorporated herein by reference in their entirety.

FIG. 1 shows the fluidic circuit for an extracorporeal blood processing system 100, used for conducting hemodialysis and hemofiltration. Referring to FIG. 1, the hemodialysis system comprises two circuits—a Blood Circuit 101 and a Dialysate Circuit 102. In one embodiment, the fluid circuits 101 and 102 are implemented in a manifold that can be used with a portable dialysis machine.

For dialysis, the patient's blood is circulated in the blood circuit 101 on one side of a semi permeable membrane (dialyzer) 103 and a dialysis liquid called the dialysate, comprising the main electrolytes of the blood in concentrations close to those in the blood of a healthy subject, is circulated on the other side in the dialysate circuit 102. The line 104 from the patient which feeds blood to the dialyzer 103 in the blood circuit 101 is provided with an occlusion detector 105 which is generally linked to a visual or audible alarm (not shown) to signal any obstruction to the blood flow. In order to prevent coagulation of blood, means 106 for injecting an anticoagulant—such as heparin, into the blood are also provided. A peristaltic pump 107 is also provided to ensure flow of blood in the normal (desired) direction.

A pressure sensor 108 is provided at the inlet where impure blood enters the dialyzer 103. Other pressure sensors 109, 110, 111 and 112 are provided at various positions in the hemodialysis system that help keep track of and maintain fluid pressure at vantage points. Also provided at the dialyzer input is the thermal flow rate sensor 150 of the present invention. The flow rate sensor, in one embodiment, comprises a plurality of contacts which help in generating a thermal signal in the fluid for flow measurement.

At the point where used dialysate fluid from the dialyzer 103 enters the dialysate circuit 102, a blood leak sensor 113 is provided to sense and prevent any leakage of blood into the dialysate circuit. A pair of bypass valves 114 is also provided at the beginning and end points of the dialysate circuit, which ensure that fluid flow is in the desired direction in the closed loop circuit. Another bypass valve 115 is provided just before a priming/drain port 116. The port 116 is used for initially preparing the circuit curves with a priming solution, and to remove used dialysate fluid during dialysis and replace portions of dialysate with replenishment fluid of appropriate sodium concentration.

The dialysate circuit is provided with two peristaltic pumps 117 and 118. Pump 117 is used for pumping out used dialysate fluid to the drain or waste container, as well as for pumping regenerated dialysate into the dialyzer 103. Pump 118 is used for pumping out spent dialysate from the dialyzer 103, and also for pumping in the replacement fluid from port 116 for maintaining sodium concentration in the dialysate.

A sorbent type cartridge 119 is provided in the dialysate circuit, which contains several layers of materials, each having a specific role in removing impurities such as urea. The combination of these materials allows water suitable for drinking to be charged into the system for use as dialysate fluid. For the fresh dialysate fluid, a lined container or reservoir 120 of a suitable capacity is provided.

Depending upon patient requirement, desired quantities of an infusate solution 121 may be added to the dialysis fluid. A peristaltic pump 122 is provided to pump the desired amount of infusate solution to the container 120. A camera 123 may optionally be provided to monitor the inflow of the infusate solution.

A heater 124 is provided to maintain the temperature of dialysate fluid in the container 120 at the required level. The temperature of the dialysate fluid can be sensed by the temperature sensor 125. The container 120 is also equipped with a scale 126 for keeping track of the weight of the fluid in the container, and a conductivity meter 127, which displays the conductivity of the dialysate fluid measured by the conductivity sensor 128. The conductivity sensor 128 provides an indication of the level of sodium in the dialysate.

A medical port 129 is provided before blood from the patient enters the system for dialysis. Another medical port 130 is provided before clean blood from the dialyzer is returned to the patient. An AIL sensor 131 and a pinch clamp 132 are employed in the circuit to ensure a smooth and unobstructed flow of clean blood to the patient. Priming sets 133 pre-attached is to the hemodialysis system that helps prepare the system before it is used for dialysis.

Figure 2:
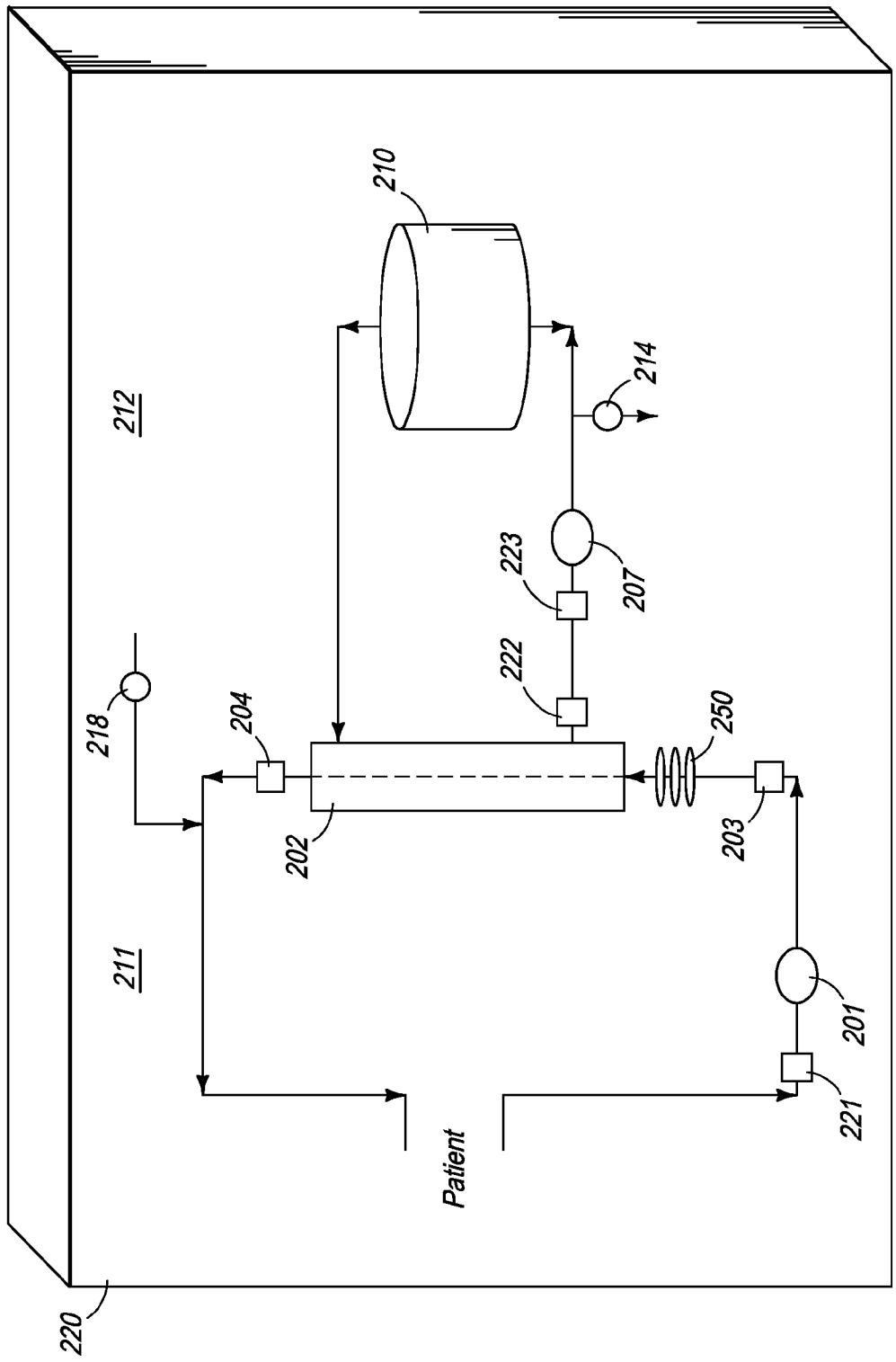
FIG. 2 is a schematic depicting a manifold with a flow rate sensor of the present invention included therein.

FIG. 2 is an illustration of one embodiment of a hemofiltration circuit. In one embodiment, as further discussed below in FIG. 3, the hemofiltration circuit comprises the blood 211 and dialysate 212 flow paths that are molded in a single compact plastic unit. All the sensors, including the thermal flow meter 250 of the present invention, the dialyzer blood inlet pressure transducer 203, the blood outlet pressure transducer 204, conductivity meters 221, 222, and leak sensor 223 are all integrated into the molding of the manifold 220. Other components, such as disposable sorbent cartridges 210, volumetric pumps 201, 207, 214 and 218, and dialyzer 202, are outside of the manifold.

Figure 3:
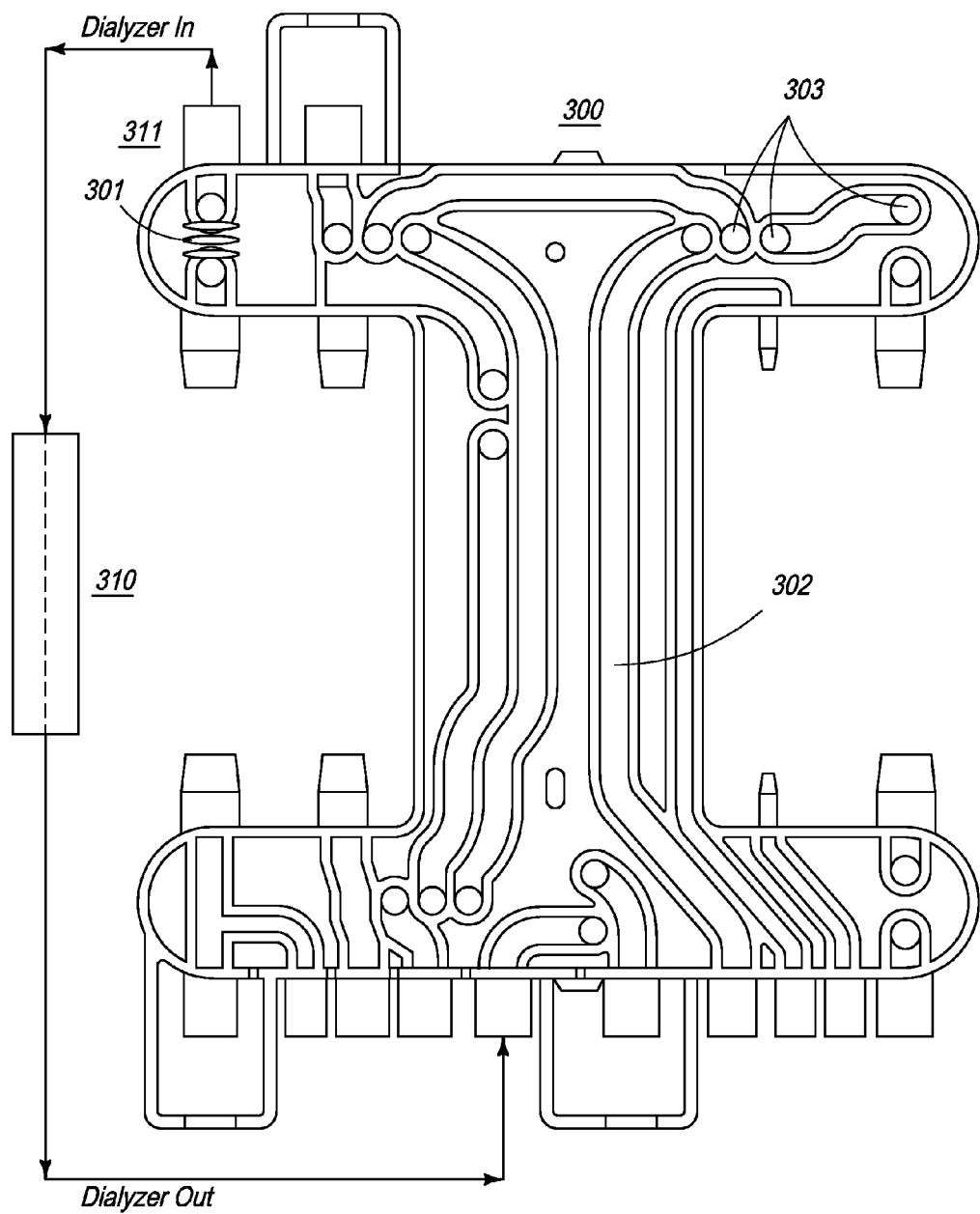
FIG. 3 provides a perspective view of the thermal flow sensor of the present invention integrated into the compact manifold.

FIG. 3 provides another perspective view of the compact manifold 300, with the thermal flow meter of the present invention integrated therein. As is shown in FIG. 3, the thermal flow meter 301 is placed at the inlet port 311 to the dialyzer 310. The complete blood and dialysate flow paths 302 of the hemodialysis/hemofiltration system are also molded into the manifold 300. Besides the thermal flow meter 301, other functional elements 303 of the blood purification system, as described above, are also integrated into the compact manifold. One of ordinary skill in the art would appreciate that the number and location of the thermal flow meter(s) that are integrated within the manifold may be varied according to the requirement and application of the blood purification system. Further, the thermal flow measurement device of the present invention may be used for any kind of fluid during dialysis, such as blood, dialysate, infusate, medications, etc. Finally, it should be appreciated that the description of the blood and dialysate circuits are for context purposes and should not be viewed as limiting to the nature, operation, or placement of the thermal flow meters of the present invention.

Figure 4:
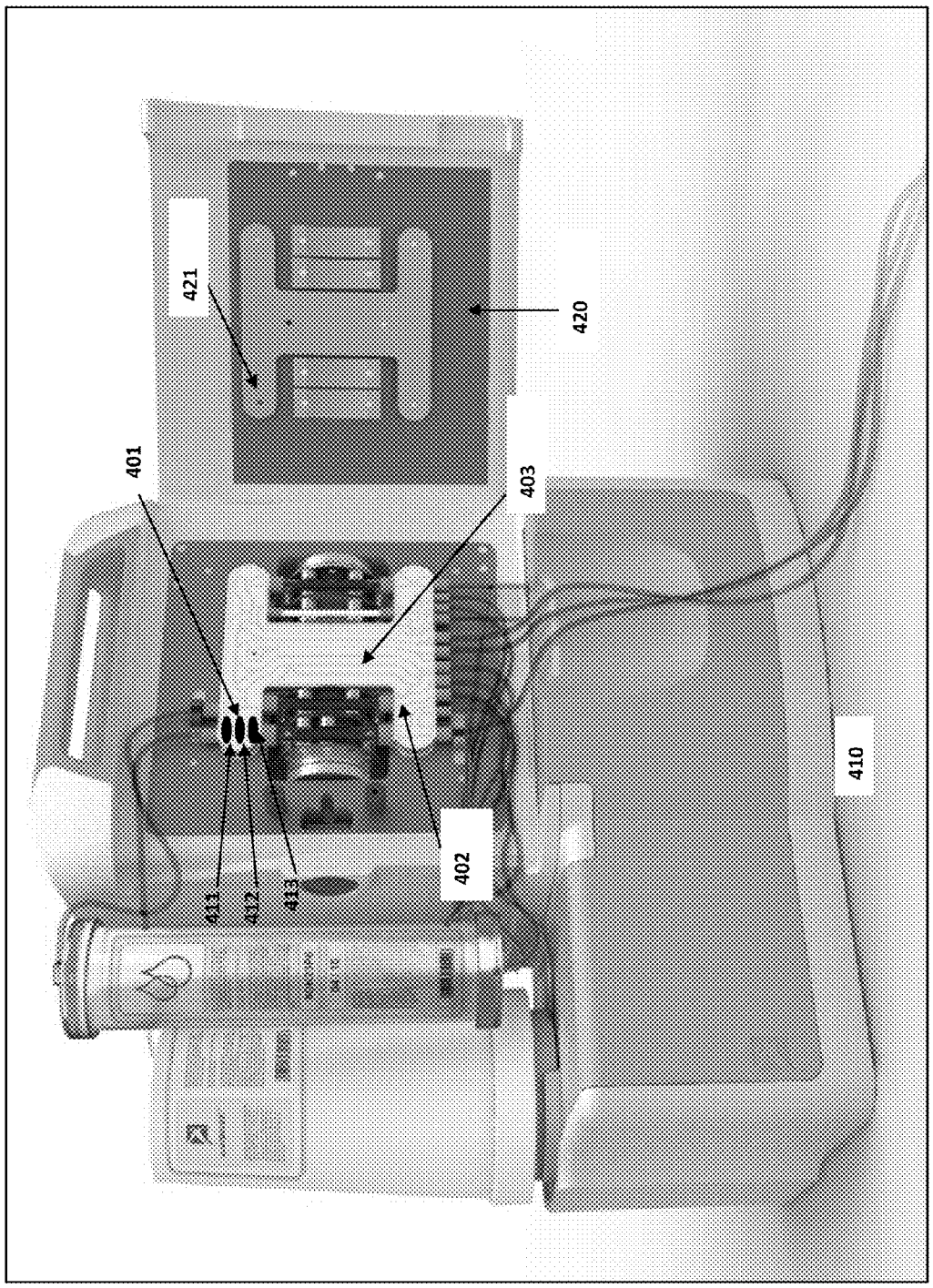
FIG. 4 illustrates the installation of the thermal flow sensor along with the compact manifold in a dialysis machine.

FIG. 4 illustrates the thermal fluid flow measurement device 401 of the present invention installed with the manifold 402 in the dialysis machine 410. As mentioned earlier, the manifold 402 has fluid flow paths or tubing circuit 403 embedded within. The dialysis machine 410 has a front door 420 which can be opened to install the disposable manifold 402. Further, the front door 420 is equipped with pins 421 that, when the door 420 is closed, can make contact with electrical points on the manifold 402 to read information or provide electrical input.

The thermal fluid flow measurement device 401 further comprises a series of contacts 411, 412 and 413. Operationally, as fluid (such as blood, dialysate or other fluids) flows during dialysis through the fluid flow path 403, it passes the first contact 411 which is embedded in the plastic pathway. The contact 411 makes electrical contact with an electrical source, which in one embodiment is a pin 421 on the machine front door 420. The electrical source or pin is controlled by a controller (not shown) in the dialysis machine 410. The electrical source provides an electrical stimulus to the contact 411, which acts to micro heat the contact based on a sinewave method. In one embodiment, the micro heating process effectuates a temperature increase between 0.1 and 1.0 degrees Celsius in the fluid being measured. This is effectuated by means of micro heaters located at the first contact 411, which produce heat on receiving the electrical stimulus. Micro heaters for the thermal fluid flow measurement device of the present invention can be manufactured using any design suitable for the application. In one embodiment for example, the micro heater is made up of 10 turns of 30 g copper wire wound around a pin located at the first contact position 411.

As the contact 411 gets micro-heated, the resulting thermal energy acts to create a thermal wave, which propagates downstream from the first contact 411. A plurality of contacts, which in one embodiment are two in number—412 and 413 are located downstream from the first contact 411, and are used to measure the time of flight of the thermal wave. The measured phase of the wave is then compared with the initial wave generated by the first contact 411. The phase difference thus determined provides an indication of the flow rate.

Figure 5A:
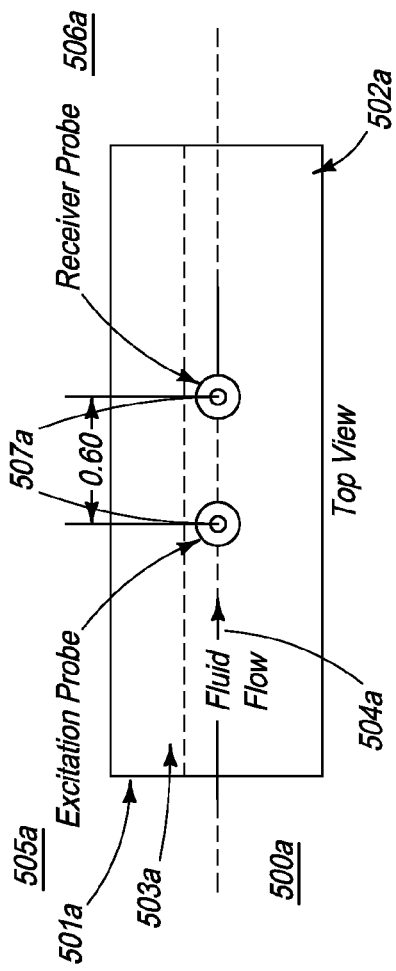
FIG. 5a is a top view schematic of one embodiment of the thermal flow meter of the present invention.
Figure 5B:
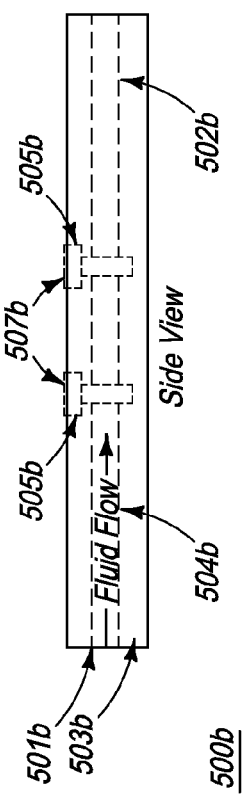
FIG. 5b is a side view schematic of one embodiment of the thermal flow meter of the present invention.
Figure 5C:
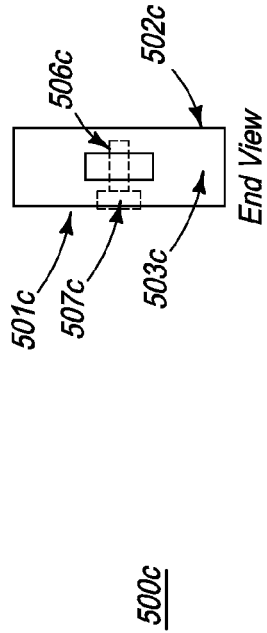
FIG. 5c is an end view schematic of one embodiment of the thermal flow meter of the present invention.

FIGS. 5a through 5c illustrate one embodiment of a flow cell with probes that can be used for flow measurement. Referring to FIG. 5a, a top view of one embodiment of the thermal flow meter 500a of the present invention is shown. A channel 501a encompasses a volume 502a through which fluid, such as water or saline solution (0.9 N) 503a flows. In one embodiment, the channel has a height in the range of 1 mm to 5 mm (preferably 3 mm), a width in the range of 3 mm to 13 mm (preferably 8 mm), a length in the range of 10 mm to 100 mm (preferably 50 mm), a channel area in the range of 3 $mm^2$ to 65 $mm^2$ (preferably 24 $mm^2$), and/or a a hydraulic diameter in the range of 1.5 mm to 7.22 mm (preferably 4.36 mm).

The direction of the fluid flow is shown by arrow 504a. An excitation probe 505a is positioned proximate to a receiver probe 506b. The distance the probes is an important feature of design, as the excitation frequency at which the electrical stimulus needs to be delivered by the excitation pin or probe 505a depends on the spacing between the probes 505a and 505b. In one embodiment, the excitation probe and receiver probe are positioned less than 2 inch, preferably less than 0.8 inches, and more preferably approximately 0.6 inches, or approximately 15 mm, from each other. In this embodiment, excitation and measurement only requires two contacts, each contact having a contact surface 507a. One of ordinary skill in the art would appreciate that, in such a case, only two contact points would be required, rather than three, as shown above relative to a disposable manifold and dialysis machine.

An excitation pin or probe 505a is embedded in the channel 501a and acts to provide a thermal stimulus (in the form of a thermal wave) to the flowing fluid, which is then sensed and measured by the receiving contact 506a. In one embodiment, the body diameter of the pin or probe is in the range of 0.03 inches to 0.15 inches (preferably 0.08 inches), the diameter of the top contact surface is in the range of 0.025 inches to 0.2 inches (preferably 0.125 inches), and is made of gold plated brass or any other material having a density of approximately 8500 kg/m³, a thermal conductivity of approximately 1.09 W/mK and/or a specific heat of approximately 0.38 J/KgK.

In one embodiment, the bodies of both the excitation pin or probe 505a and the receiving pin or probe 506a are molded into the manifold (such that the pin or probe is not physical contact with the fluid and its top contact area is exposed to one surface of the manifold). The body of the pin or probe is centered in the cell and fluid passes by it. The top of the pin is exposed so a spring loaded contact, from the instrument panel, can make thermal contact, thereby enabling the transfer of thermal energy between the spring loaded contact and the contact surface of the pin.

For example, referring to FIG. 5b, a side view of one embodiment of the thermal flow meter 500b of the present invention is shown with the contact surface 507b exposed so that a spring loaded contact from the instrument panel of the dialysis machine (shown in FIG. 4) can make thermal contact and thermal energy can be exchanged between the spring loaded contact and the excitation pin or probe 505b. A channel 501b encompasses a volume 502b through which fluid 503b flows. The direction of the fluid flow is shown by arrow 504b. An excitation probe 505b is positioned proximate to a receiver probe 506b, each of which has a contact surface 507b.

FIG. 5c shows thermal flow meter 500c from the end of the flow channel 501c, which contains a volume 502c through which fluid 503c flows. Here, only the receiver probe 506c and its contact surface 507c is shown. In one embodiment, the receiving contact or pin 506c has a structure similar to that of the excitation pin 505c and its top 507c is also exposed. In one embodiment, the receiver pin surface 507c is also designed as a low thermal mass spring loaded contact. The excitation 505a as well as receiver 505a probes or pins are made up of a suitable material which has high thermal and electrical conductivity, which in one embodiment is gold plated brass.

In one embodiment, a low thermal mass spring loaded contact in the instrument, such as a dialysis machine, is temperature controlled using a heater and a thermistor. The temperature control function then generates a cosine temperature wave form in the probe which is reflective of the temperature wave created in the spring loaded contact. The resultant excitation signal characteristic of the excitation pin may be defined as:

$e_s = E_s \cos(\omega t)$, where $\omega t$ is the excitation frequency.

The thermal response of the receiver pin may be characterized by the following equation:

$r_r = R_r \sin(\omega t + \theta)$, where $\omega t$ is the excitation frequency and $\theta$ is the phase.

One representation of the propagation of a thermal wave is shown in FIGS. 6a and 5b. Referring to FIG. 6a, the arrow 601 represents the direction of flow of fluid (and hence the direction of propagation of a thermal wave) in a fluid pathway 602 in a channel. Measurement contacts are represented by 611, 612 and 613. Since the micro heater (not shown) is located proximate to the first contact 611, the thermal wave originates at the first contact, and then propagates towards the second and third contacts 612 and 613 respectively, which are located downstream from the first contact 611. The distance between the second 612 and third 613 contacts is 615.

FIG. 6b illustrates exemplary wave measurements at the three contacts 611, 612 and 613 of FIG. 6a. Referring to FIGS. 6a and 6b, the thermal wave generated at the first contact 611 is represented by the first curve 621. Given that the flow is from left to right, this thermal wave will reach contact 612 at the second location slightly ahead of the time than when it reaches the contact 613 at the third location. The outputs of the second and third contacts 612 and 613 are represented by the curves 622 and 623, respectively.

The phase shift between the second 622 and third 623 signals can be measured by comparing the points of the zero crossing for each. The distance 615 between the second 612 and third 613 contacts divided by the time between the respective zero crossings (also called time of flight) is equal to the flow velocity of the fluid. Further, multiplying the computed flow velocity by the diameter of the fluid pathway yields the volume flow rate.

The thermal wave can be monitored by using temperature sensors, which in one embodiment are constructed of thermistors, such as Cantherm, part number, CWF4B153F3470, and are placed in physical contact with contacts located at the second and third positions. In one embodiment, the contacts are monitored/measured using thermal measuring devices (which are in contact with the two metal contacts) in the dialysis machine itself. This eliminates the need for separate temperature measuring devices to be integrated in the manifold. It should be appreciated that, in a preferred embodiment, a dialysis machine, or non-disposable instrument, contains a processor and a memory which record a) the excitation frequency communicated to the spring loaded contact which, upon installation of a disposable manifold, physically communicates with the contact surface of the excitation probe and b) the frequency of the temperature wave sensed by the receiver probe and communicated, through the contact surface of the receiver probe, to a spring loaded contact in the dialysis machine, or non-disposable instrument. The processor implements the derivations, described herein, to determine the temperature levels and changes based upon the above-listed stored data. It should be further appreciated that this temperature information is then communicated to a display driver which causes the information to be visually displayed, or audibly communicated, via a user interface.

In one embodiment, the detection circuit examines the phase shift by mixing the excitation signal and receiver signal, performing a comparison, and subjecting the result to a low pass filter in order to get the phase shift information. More specifically, in one embodiment, phase detection is accomplished by multiplying the excitation frequency by the receiver signal. The results yield a signal with two components, one at twice the frequency and one being a DC signal proportional to the phase shift between the excitation reference signal and the receiver signal. This is represented by the following equation:

$$\text{Phase Detection}: e_s r_r = \frac{E_s R_r}{2}[\sin(2\omega t + \theta) + \sin\theta]$$

Where $e_s$ is the excitation signal, $r_r$ is the receiver signal, $\omega t$ is the excitation frequency and $\theta$ is the phase.

As described above, the present invention relies on a wave for time of flight measurement and not a thermal pulse. This method offers a significant advantage because a thermal pulse disperses, resulting in uncertainty over where the pulse edge begins, and substantially increases the measurement noise. Waves disperse as well but the phase shifts of a sine wave, even after dispersion, remain more distinct. Therefore relying on sine wave for measurement introduces less noise.

Another advantage of the present invention lies in integrating the thermal flow rate sensor in the disposable manifold. The plastic used in the manifold acts as a thermal insulator, which beneficially affects measurements. As mentioned previously, in one embodiment spring-loaded probes are used for the thermal flow measurement device, which makes it low cost and disposable.

The design of the device of present invention is optimized in accordance with three parameters: a) thermal excitation (frequency of the thermal input signal), b) the expected flow rate (a slower flow rate requires a different frequency than a higher flow rate because a slower flow rate experiences dispersion more), and c) amount and extent of thermal dispersion. In one embodiment, in order to minimize noise and improve detection accuracy, one can set a key parameter as being constant, e.g. constant phase shift, constant frequency, or constant flow area.

In one embodiment, the constant phase shift method is implemented by using a phase sensitive detector and a digitally controlled frequency generator. As described above, the time of flight causes a physical delay between the excitation probe and the receiver probe. At high flow rates the physical delay is small, while at low flow rates, the physical delay is large. Therefore, in order to maintain a constant phase shift the excitation frequency is controlled via feedback from the phase sensitive detector. A feedback loop is included in the system so that important parameters such as excitation frequency can be dynamically adjusted such that the phase shift remains constant.

Figure 11:
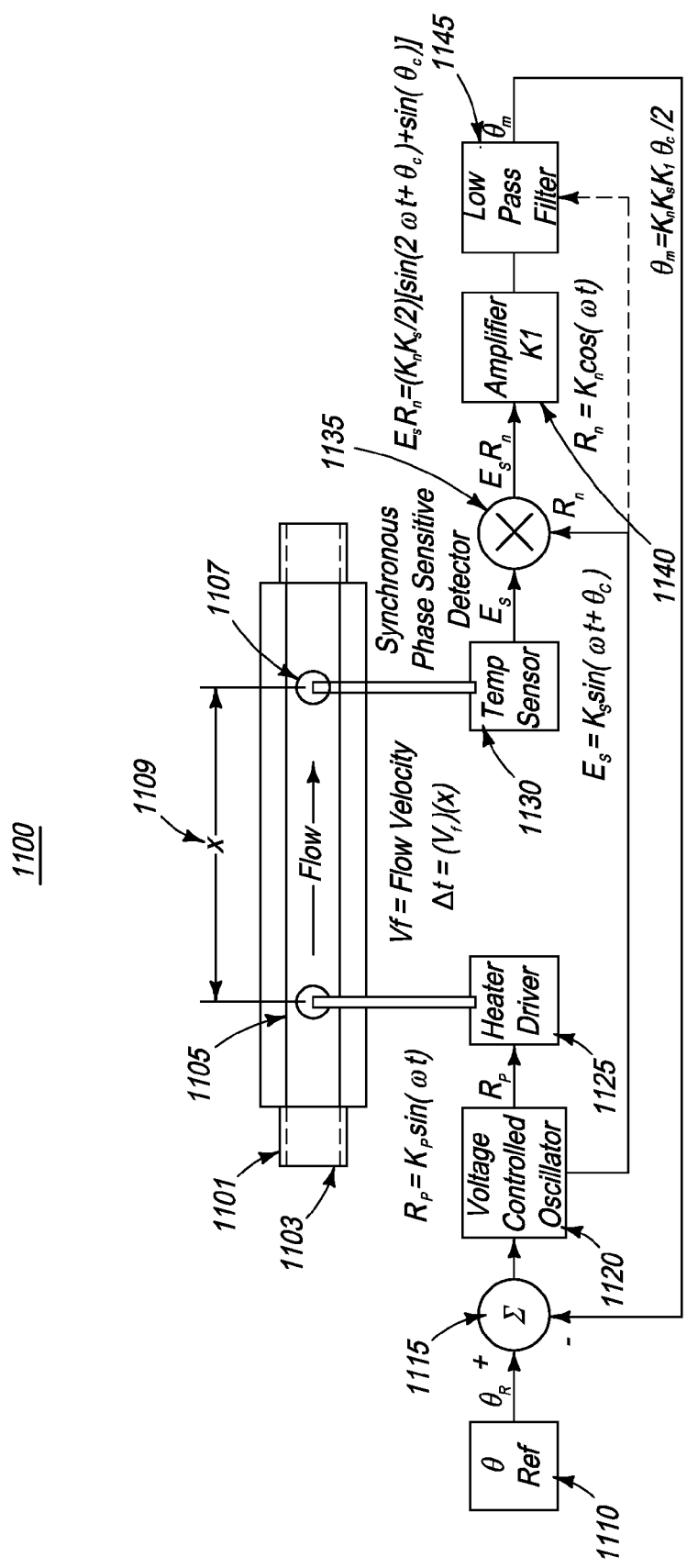
FIG. 11 is a schematic of one embodiment of the present invention employing a constant phase mode of operation.

Referring to FIG. 11, a schematic of one embodiment of the present invention employing a constant phase shift mode of operation is shown. Liquid 1103 flowing through a channel 1101 passes by excitation probe 1105 and receiver probe 1107, which are separated by a distance 1109, as described above. In one embodiment, the channel 1101 is part of a manifold which is designed to be inserted into, and used within, a dialysis machine. Once installed within the dialysis machine, the contact surface of the excitation probe 1105 is made to thermally contact a heater driver 1125 and the contact surface of the receiver probe 1130 is made to thermally contact a temperature sensor 1130. The heater driver 1125 and temperature sensor 1130 are in electrical contact with a circuit, embodied in and/or integrated within, the dialysis machine.

On the excitation probe side, the circuit comprises a reference signal source 1110 which transmits a signal having a phase $\theta r$ to a summation device 1115, which also receives a signal input $\theta m$ from a low pass filter, as described below. The two signals are summed, processed, or otherwise compared to yield an output which is transmitted to a voltage controlled oscillator 1120. The voltage controlled oscillator 1120 outputs a signal, Rp where $Rp=Kp \sin(\omega t)$, that is received by a heater driver 1125 and used to drive the heater driver 1125 to yield the excitation wave which is thermally communicated to probe 1105.

The thermal wave propagates through the channel 1101 as a function of the fluid 1103 flow rate. The receiver probe 1107 which thermally communicates the sensed thermal wave to the temperature sensor 1130. The thermal sensed wave can be expressed as a function as follows: $Es=Ks \sin(\omega t+\theta c)$.

As stated above, the temperature sensor 1130 is in electrical contact with a circuit embodied within, or integrated into, the dialysis machine. The sensed thermal wave (Es) is communicated to a synchronous phase sensitive detector employing a multiplier component 1135, which multiplies the sensed thermal wave (Es) with an input signal from the voltage controlled oscillator 1120 (Rn, where $Rn=Kn \cos(\omega t)$), yielding an output signal EsRn. Output signal EsRn (which can be expressed as $EsRn=(KnKs/2)[\sin(2\omega t+\theta c)+\sin(\theta c)]$) is input into the amplifier 1140 and amplified by constant K1. The amplified signal is then input into a low pass filter 1145, which receives an input signal from the voltage controlled oscillator 1120. The input signal from the voltage controlled oscillator 1120 is used to vary the filter threshold, or cutoff, of the low pass filter 1145. The output from the low pass filter 1145 ($\theta m$ which can be expressed as a function of $KnKsK1\theta c/2$) is a signal that is indicative of the flow rate of the fluid, which can be derived by any means known to persons of ordinary skill in the art, and is communicated back to said summation device 1115 for use in generating the reference signal from the voltage controlled oscillator 1120.

FIG. 7a is a table which illustrates the range of excitation frequency that is dynamically adjusted to maintain a constant phase shift. Referring to FIG. 7, the determination process takes into account the values of various parameters such as flow rate 701, which varies between 25 to 600 ml/min and flow velocity 702 which ranges from 17.36 mm/s to 416.67 mm/s. Using a 15 mm value for probe separation 703, the excitation frequency 705 will vary from ~1.16 Hz @25 mL/min flow rate to 27.78 Hz @600 mL/min flow rate. The corresponding values of travel time and receiver amplitude are detailed in rows 704 and 706, respectively. Note that receiver amplitude is maintained at zero for a constant phase shift.

Figure 7B:
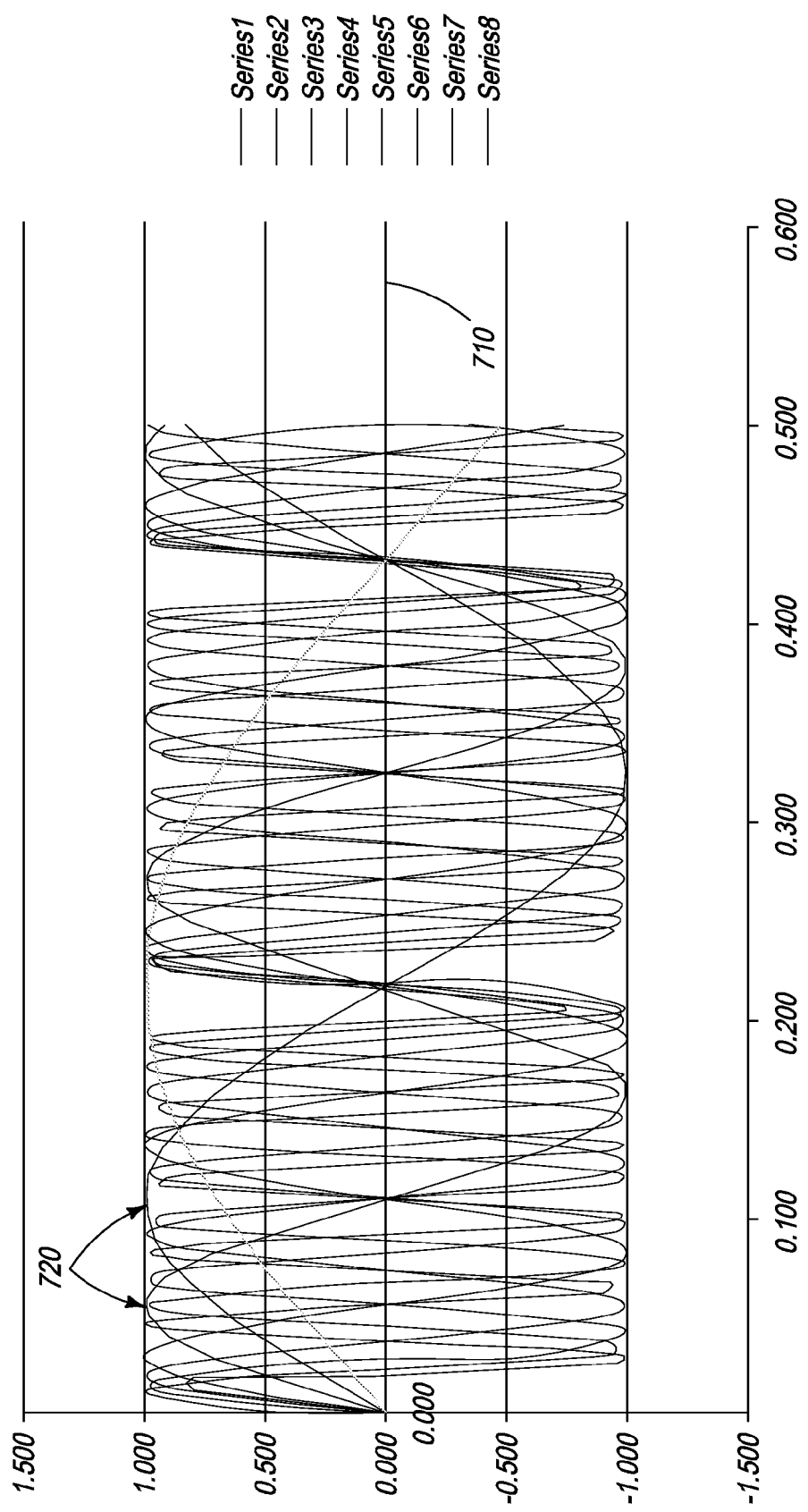

FIG. 7b illustrates the output of the phase sensitive detector plotted against time axis 710. The various curves 720 represent a series of outputs of the phase sensitive detector for different values of flow rate. The graphs in FIG. 7b have been plotted for the values given in the table of FIG. 7a; accordingly, the flow rate ranges from 25 to 600 ml/min and the corresponding excitation frequency varies from ~1.16 Hz to 27.78 Hz.

Figure 8B:
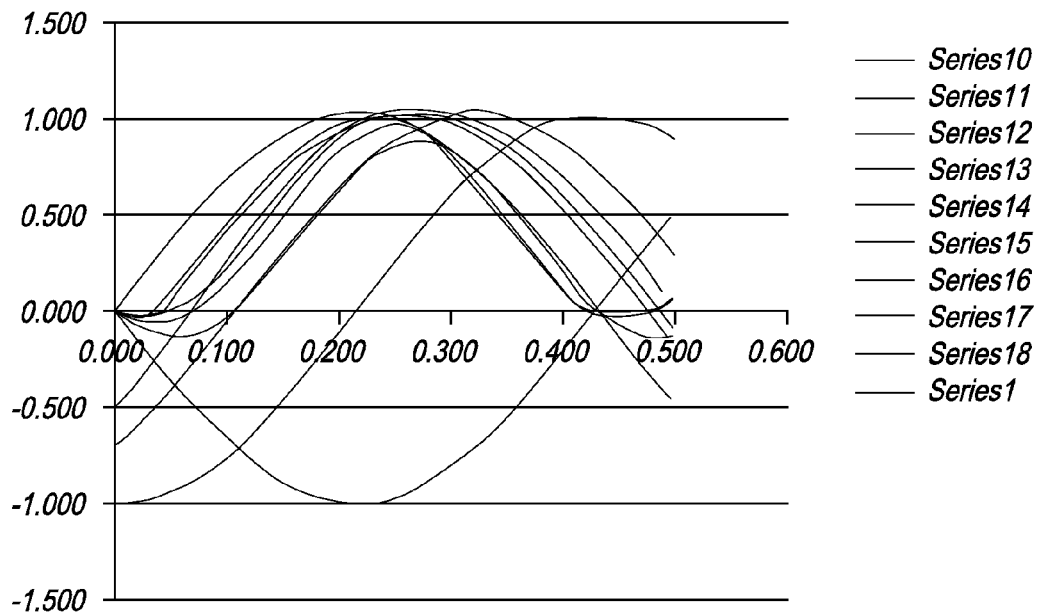
FIG. 8b illustrates two sets of outputs for the range of values specified in FIG. 8a of the phase sensitive detector.
Figure 8C:
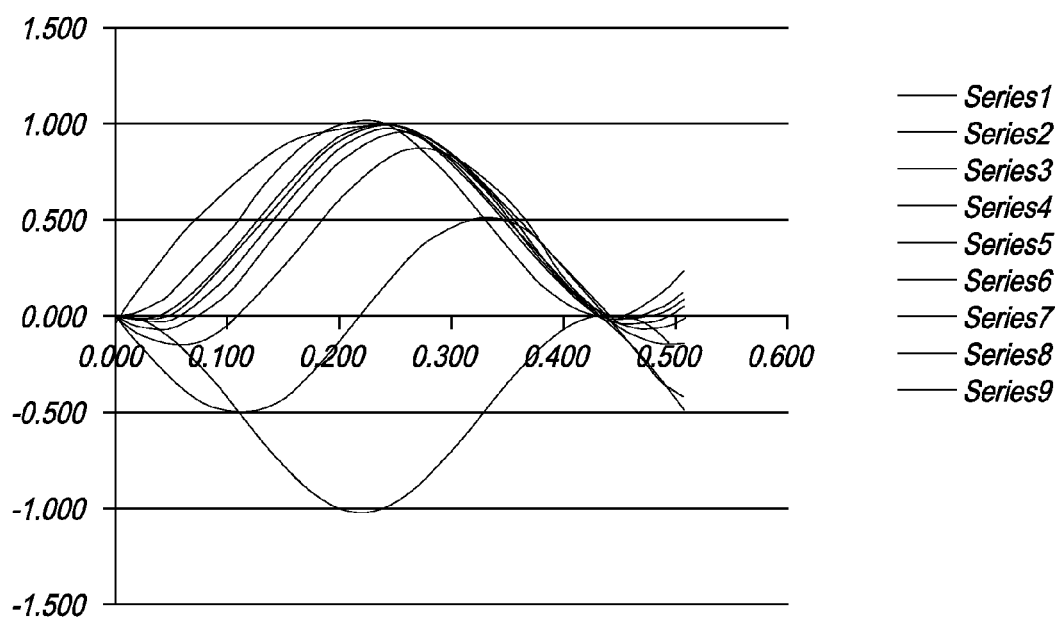
FIG. 8c illustrates two sets of outputs for the range of values specified in FIG. 8a of the phase sensitive detector.

In another embodiment, phase shift may be allowed to vary while the frequency excitation remains constant. Constant frequency excitation is employed along with a phase sensitive detector, while a feedback mechanism is not used. FIG. 8a illustrates a table detailing values of various parameters when the excitation frequency 806 is maintained at 1.157 Hz. This value is for flow rate 801 varying between 25 to 600 ml/min and flow velocity 802 ranging from 17.36 mm/s to 416.67 mm/s. While the probe separation 803 is set at 15 mm, the corresponding values of travel time 804 range from 0.0360 sec (for Harmonic 805 value of 1.000) to 0.864 sec. Varying phase shift is reflected in the corresponding receiver amplitude values detailed in row 806. FIGS. 8b and 8c illustrate two sets of outputs (for the range of flow rates specified in FIG. 8a) of the phase sensitive detector plotted against time axis.

Figure 12:
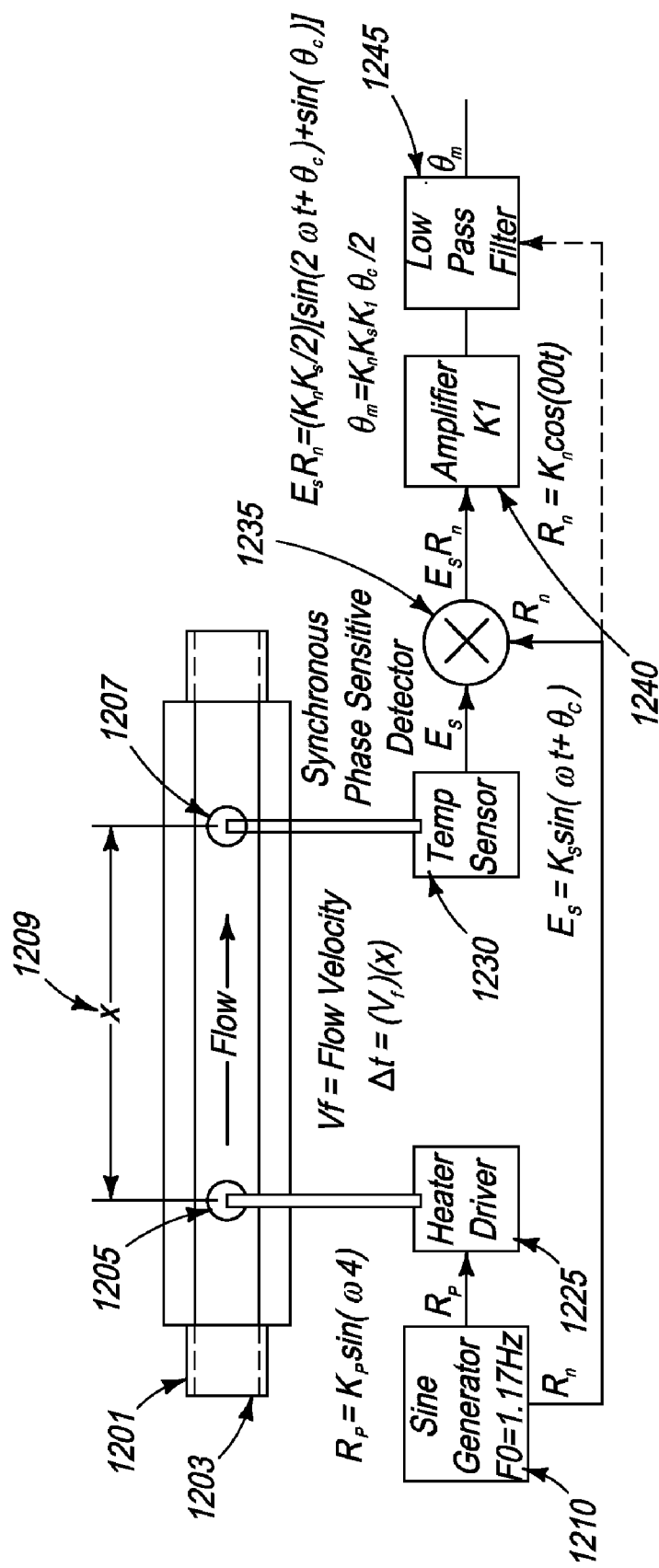
FIG. 12 is a schematic of one embodiment of the present invention employing a constant frequency mode of operation.

Referring to FIG. 12, a schematic of one embodiment of the present invention employing a constant frequency mode of operation is shown. Liquid 1203 flowing through a channel 1201 passes by excitation probe 1205 and receiver probe 1207, which are separated by a distance 1209, as described above. In one embodiment, the channel 1201 is part of a manifold which is designed to be inserted into, and used within, a dialysis machine. Once installed within the dialysis machine, the contact surface of the excitation probe 1205 is made to thermally contact a heater driver 1225 and the contact surface of the receiver probe 1230 is made to thermally contact a temperature sensor 1230. The heater driver 1225 and temperature sensor 1230 are in electrical contact with a circuit, embodied in and/or integrated within, the dialysis machine.

On the excitation probe side, the circuit comprises a reference signal source 1210, such as a sine generator, which transmits a signal having a frequency (e.g. at or about 1.17 Hz) to a heater driver 1225. The sine generator 1210 outputs a signal, Rp where Rp=Kp sin($\omega$t), that is received by a heater driver 1225 and used to drive the heater driver 1225 to yield the excitation wave which is thermally communicated to probe 1205. It is preferred that the excitation frequency is low enough so at low flow rates the phase shift is less than 80 degrees. The sine generator 1210 also outputs a signal, Rn where Rn=Kn cos($\omega$t), that is received by a multiplier 1235 and low pass filter 1245, as further described below.

The thermal wave propagates through the channel 1201 as a function of the fluid 1203 flow rate. The receiver probe 1207 which thermally communicates the sensed thermal wave to the temperature sensor 1230. The thermal sensed wave can be expressed as a function as follows: Es=Ks sin($\omega$t+$\theta$c). The temperature sensor 1230 is in electrical contact with a circuit embodied within, or integrated into, the dialysis machine. The sensed thermal wave (Es) is communicated to a synchronous phase sensitive detector employing a multiplier component 1235, which multiplies the sensed thermal wave (Es) with an input signal from the sine generator 1210 (Rn, where Rn=Kn cos($\omega$t)), yielding an output signal EsRn. Output signal EsRn (which can be expressed as EsRn=(KnKs/2)[sin (2$\omega$t+$\theta$c)+sin($\theta$c)]) is input into the amplifier 1240 and amplified by constant K1. The amplified signal is then input into a low pass filter 1245, which receives an input signal from the sine generator 1210. The input signal from the sine generator 1210 is used to vary the filter threshold, or cutoff, of the low pass filter 1245. The output from the low pass filter 1245 ($\theta$m which can be expressed as a function of KnKsK1$\theta$c/2) is a signal that is indicative of the flow rate of the fluid, which can be derived by any means known to persons of ordinary skill in the art. It should be appreciated that the frequency cutoff of the low pass filter is approximately 1/20 of the frequency of the excitation frequency. The low pass filter should attenuate the 2$\omega$t signal by at least 80 db.

Figure 13:
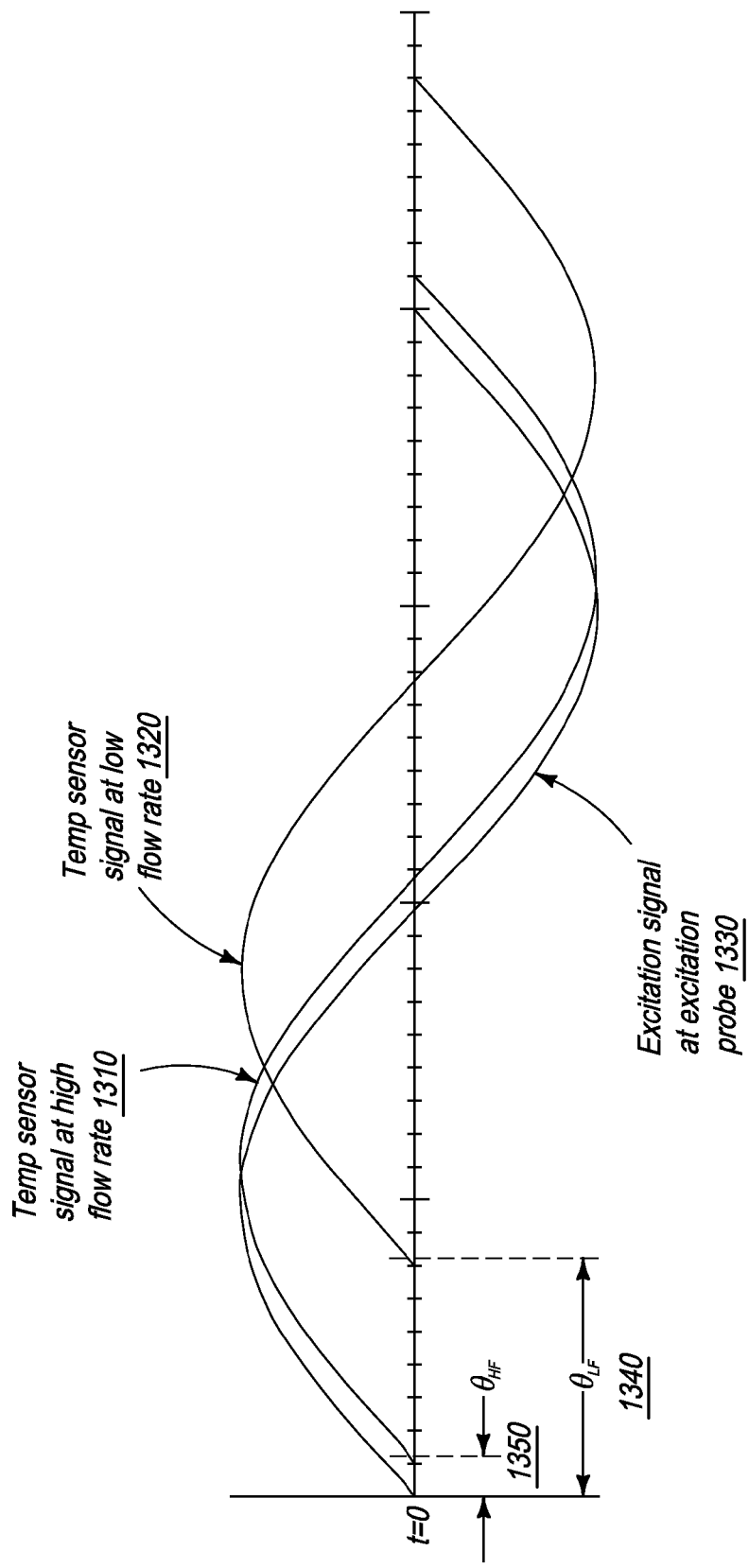
FIG. 13 is a graph of signals generated in a constant frequency mode of operation.

FIG. 13 shows the relative phase shifts of signals generated in the constant frequency mode with a low flow rate and a high flow rate. An excitation signal 1330 is generated at time 0. In a low flow rate scenario, the sensed signal 1320 is offset from the excitation signal 1330 by a phase shift of $\theta_{LF}$ 1340 while, in a high flow rate scenario, the sensed signal 1310 is offset from the excitation signal 1330 by a phase shift of $\theta_{hF}$ 1350.

Regardless of whether constant or varying phase shift method is employed for measurement, using phase shift as the basis of flow measurement is advantageous as compared to using amplitude, since amplitude can get affected by external factors such as external temperature influences, which should not affect the phase shift.

In one embodiment, the non-invasive thermal fluid flow meter of the present invention provides a measurement range of 20 mL/min to 600 mL/min. Besides the factors listed previously, other factors that are important for designing the thermal flow meter for optimum performance include flow characteristics such as flow regime, maximum Reynolds number and flow velocity; and physical characteristics of the flow cell, such as channel height, width and length.

FIG. 9 comprises a table delineating an exemplary set of design parameters optimized such that the flow regime is kept laminar and Reynold's number 909 is maintained under 2000, for a maximum flow rate 901 of 600 ml/min. For keeping the flow regime laminar, channel size—including channel height 902, width 903, length 904, area 905 and hydraulic diameter 906 are optimized. Reynold's number 909 is computed after taking into account values of flow velocity 907, hydraulic diameter 906 and properties of water 908, such as density, dynamic viscosity and kinematic viscosity.

In one embodiment, the flow cell is designed for turbulent flow regime instead of laminar. Such a design of the flow cell entails a constant flow area, which in turn would involve the flow area being widened around the probes (which is reduced around the probes for laminar flow). When the area at the probes widens, the fluid increases in velocity around the probes and the increased velocity causes the flow regime to move into the turbulent regime.

FIG. 10 is a table illustrating another set of exemplary design parameters for the excitation and receiver probes, which in one embodiment are sized to have a thermal time constant 1005 under 1 millisecond for optimum performance. The factors taken into account for this purpose are the material—which in this case is brass, and its properties 1001 such as density, thermal conductivity and specific heat, as well as convection coefficient 1004. Accordingly the size 1002 and exposed surface area 1003 of the probes is determined.

Hereinbefore has been disclosed a system and method of non-invasively measuring the rate of flow of fluid passing through a passageway using a photo-acoustic flow meter of the present invention. It will be understood that various changes in the details, arrangement of elements and operating conditions which have been herein described and illustrated in order to explain the nature of the invention may be made by those skilled in the art without departing from the principles and scope of the invention. Therefore, the present examples and embodiments are to be considered as illustrative and not restrictive, and the invention may be modified within the scope of the appended claims.

We claim:

1. A flow rate sensor for sensing the flow rate of a fluid passing through a channel of a disposable manifold that is installed in a dialysis machine, comprising:
   a. An excitation probe having a body and a contact surface, wherein said excitation probe is integrated within said disposable manifold and physically positioned within said channel and the excitation probe generates a thermal wave within said fluid in response to a first electrical signal;
   b. A receiver probe having a body and a contact surface, wherein said receiver probe is integrated within said disposable manifold and physically positioned within said channel and wherein said receiver probe senses a thermal wave within said fluid;
   c. A reference signal generator, wherein said reference signal generator outputs a reference signal;
   d. A heat source in said dialysis machine, wherein said heat source receives said reference signal from said reference signal generator, comprises a contact surface that is on a surface of a portion of said dialysis machine and is configured to electrically engage with said excitation probe only when said portion of said dialysis machine is placed in physical contact with said disposable manifold, and generates said first electrical signal, having a frequency derived from said reference signal;
   e. A temperature sensor in said dialysis machine, wherein said temperature sensor comprises a contact surface that is on the surface of the portion of said dialysis machine and is configured to thermally engage with said receiver probe only when said portion of said dialysis machine is placed in physical contact with said disposable manifold, and generates a second electrical signal, having a frequency derived from said thermal wave;

f. A multiplier for receiving an input signal from said reference signal generator, for receiving said second electrical signal and for outputting a third signal; and g. A filter for receiving a fourth signal, wherein said fourth signal is a function of the third signal, and for receiving an input signal from said reference signal generator, wherein said low pass filter modulates its cutoff frequency based upon the input signal from said reference signal generator.

2. The flow rate sensor of claim 1 wherein said receiver probe is separated from said excitation probe by a distance of less than two inches.

3. The flow rate sensor of claim 1 further comprising an amplifier for amplifying said third signal and generating said fourth signal.

4. The flow rate sensor of claim 1 wherein said channel area is in the range of 3 mm$^2$ to 65 mm$^2$.

5. The flow rate sensor of claim 1 wherein the body of said receiver probe or excitation probe has a diameter in the range of 0.03 inches to 0.15 inches.

6. The flow rate sensor of claim 1 wherein the contact surface of said receiver probe or excitation probe has a diameter in the range of 0.025 inches to 0.2 inches.

7. The flow rate sensor of claim 1 wherein the excitation probe and receiver probe are embedded into a manifold and wherein the contact surfaces of said receiver probe or excitation probe are externally exposed.

8. The flow rate sensor of claim 1 wherein said filter is a low pass filter.

9. The flow rate sensor of claim 8 wherein the low pass filter generates a filtered signal and wherein the reference signal generator generates said reference signal based, at least in part, on said filtered signal.

10. The flow rate sensor of claim 1 wherein the flow rate sensor has an operative sensing range between 20 mL/min to 600 mL/min.

11. The flow rate sensor of claim 1 wherein said flow rate sensor dynamically adjusts said reference signal in order to maintain a constant phase.

12. A dialysis system comprising a flow rate sensor for sensing a flow rate of a fluid passing through a channel in a disposable manifold having a hydraulic diameter in a range of 1.5 mm to 7.22 mm, wherein said disposable manifold is adapted to be detachably installed in said dialysis system, comprising:

a. At least two probes, each having a body embedded into a first surface of said manifold and positioned within said channel and each probe having a contact surface positioned on a surface of said disposable manifold, wherein a first of said at least two probes generates a thermal wave within said fluid in response to a first electrical signal and a second of said at least two probes senses said thermal wave within said fluid;

b. A reference signal generator, wherein said reference signal generator outputs a reference signal;

c. A heat source in said dialysis machine, wherein said heat source receives said reference signal from said reference signal generator, comprises a contact surface that is on a surface of a portion of said dialysis machine and is configured to electrical engage with the first of said at least two probes only when said ortion of said dial sis machine is placed in physical contact with said disposable manifold, and generates said first electrical signal, having a phase derived from said reference signal;

d. A temperature sensor in said dialysis machine, wherein said temperature sensor comprises a contact surface that is on the surface of the portion of said dialysis machine and is configured to thermally engage with said second probe only when said portion of said dialysis machine is placed in physical contact with said disposable manifold, and generates a second electrical signal, having a phase derived from said thermal wave;

e. A multiplier for receiving an input signal from said reference signal generator and for receiving said second thermal signal and for outputting a third signal; and f. A low pass filter for receiving a signal derived from said third signal, and for receiving the reference signal from said reference signal generator, wherein said low pass filter modulates its cutoff frequency based upon the reference signal.

13. The dialysis system of claim 12 wherein said second probe is separated from said excitation probe by a distance of less than two inches.

14. The dialysis system of claim 12 further comprising an amplifier for amplifying said third signal and generating the signal derived from said third signal.

15. The dialysis system of claim 12 wherein the body of each of said at least two probes has a diameter in the range of 0.03 inches to 0.15 inches.

16. The dialysis system of claim 12 wherein the contact surface of each of said at least two probes has a diameter in the range of 0.025 inches to 0.2 inches.

17. The dialysis system of claim 12 wherein said second probe comprises a thermistor.

18. The dialysis system of claim 12 wherein the low pass filter generates a filtered signal and wherein the reference signal generator generates said reference signal based, at least in part, on said filtered signal.

19. The dialysis system of claim 12 wherein said flow rate sensor dynamically adjusts said reference signal in order to maintain a constant frequency.

20. The dialysis system of claim 12 wherein said flow rate sensor dynamically adjusts said reference signal in order to maintain a constant phase.

* * * * *